(12) United States Patent
Lu

(10) Patent No.: US 10,752,904 B2
(45) Date of Patent: Aug. 25, 2020

(54) EXTENSIBLE RECOMBINASE CASCADES

(71) Applicant: Massachusetts Institute of Technology, Cambridge, MA (US)

(72) Inventor: Timothy Kuan-Ta Lu, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 121 days.

(21) Appl. No.: 15/497,703

(22) Filed: Apr. 26, 2017

(65) Prior Publication Data

US 2017/0306336 A1 Oct. 26, 2017

Related U.S. Application Data

(60) Provisional application No. 62/327,479, filed on Apr. 26, 2016.

(51) Int. Cl.
| | |
|---|---|
| *C12N 15/09* | (2006.01) |
| *C12N 15/63* | (2006.01) |
| *C12N 15/85* | (2006.01) |
| *C12N 15/90* | (2006.01) |
| *C12Q 1/6876* | (2018.01) |
| *C12N 15/10* | (2006.01) |
| *A01K 67/027* | (2006.01) |

(Continued)

(52) U.S. Cl.
CPC ........ *C12N 15/635* (2013.01); *A01K 67/0275* (2013.01); *C12N 9/1241* (2013.01); *C12N 9/22* (2013.01); *C12N 15/102* (2013.01); *C12N 15/63* (2013.01); *C12N 15/85* (2013.01); *C12N 15/902* (2013.01); *C12Q 1/6876* (2013.01); *A01K 2217/05* (2013.01); *C12N 2800/30* (2013.01); *C12N 2830/002* (2013.01); *C12Q 2600/158* (2013.01)

(58) Field of Classification Search
CPC ............ A01K 67/0275; A01K 2217/00; A01K 2217/05; A01K 2217/20; A01K 2217/203; A01K 2267/00; C12N 15/09; C12N 15/63; C12N 15/85; C12N 15/90; C12N 15/102; C12N 15/635; C12N 15/902; C12N 2800/30; C12N 2830/002; C12Q 1/6876

See application file for complete search history.

(56) References Cited

U.S. PATENT DOCUMENTS 8,645,115 B2 * 2/2014 Collins .................. C12N 15/63
703/11
8,697,359 B1 4/2014 Zhang
(Continued)

FOREIGN PATENT DOCUMENTS

EP 1134287 A1 9/2001
EP 1264891 A1 12/2002
(Continued)

OTHER PUBLICATIONS

Nissinn et al, Molecular Cell 554: 698-710, 2014.*
(Continued)

*Primary Examiner* — Kevin K Hill
(74) *Attorney, Agent, or Firm* — Wolf, Greenfield & Sacks, P.C.

(57) ABSTRACT

Provided herein are genetic constructs comprising genetic perturbation cassettes and methods of using such to assess the timing and order of gene expression.

20 Claims, 7 Drawing Sheets

Specification includes a Sequence Listing.

(51) Int. Cl.
*C12N 9/12* (2006.01)
*C12N 9/22* (2006.01)

(56) References Cited

U.S. PATENT DOCUMENTS

2004/0231006 A1 11/2004 Silver et al.
2013/0034907 A1* 2/2013 Collins .................. C12N 15/63
435/455

FOREIGN PATENT DOCUMENTS

WO WO 2013/176772 A1 11/2013
WO WO 2014/093694 A1 6/2014
WO WO 2015/153940 A1 10/2015

OTHER PUBLICATIONS

Brocard et al., A chimeric Cre recombinase inducible by synthetic, but not by natural ligands of the glucocorticoid receptor. Nucleic Acids Res. Sep. 1, 1998;26(17):4086-90.
Bunting et al., Targeting genes for self-excision in the germ line. Genes Dev. Jun. 15, 1999;13(12):1524-8.
Feil et al., Regulation of Cre recombinase activity by mutated estrogen receptor ligand-binding domains. Biochem Biophys Res Commun. Aug. 28, 1997;237(3):752-7.
Indra et al., Temporally-controlled site-specific mutagenesis in the basal layer of the epidermis: comparison of the recombinase activity of the tamoxifen-inducible Cre-ER(T) and Cre-ER(T2) recombinases. Nucleic Acids Res. Nov. 15, 1999;27(22):4324-7.
PCT/US2017/029572, Nov. 8, 2018, International Preliminary Report on Patentability.
PCT/US2017/029572, Jun. 21, 2017, International Search Report and Written Opinion.
Chavez et al., Highly efficient Cas9-mediated transcriptional programming. Nat Methods. Apr. 2015;12(4):326-8. doi: 10.1038/nmeth.3312. Epub Mar. 2, 2015.
Farzadfard et al., Tunable and multifunctional eukaryotic transcription factors based on CRISPR/Cas. ACS Synth Biol. Oct. 18, 2013;2(10):604-13. doi: 10.1021/sb400081r. Epub Sep. 11, 2013.
Gilbert et al., Genome-Scale CRISPR-Mediated Control of Gene Repression and Activation. Cell. Oct. 23, 2014;159(3):647-61. doi: 10.1016/j.cell.2014.09.029. Epub Oct. 9, 2014.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Pagliuca et al., How to make a functional β-cell. Development. Jun. 2013;140(12):2472-83. doi: 10.1242/dev.093187.
Ran et al., Genome engineering using the CRISPR-Cas9 system. Nat Protoc. Nov. 2013;8(11):2281-2308. doi:10.1038/nprot.2013.143. Epub Oct. 24, 2013.
Tanenbaum et al., A protein-tagging system for signal amplification in gene expression and fluorescence imaging. Cell. Oct. 23, 2014;159(3):635-46. doi: 10.1016/j.cell.2014.09.039. Epub Oct. 9, 2014.
Upadhyay et al., RNA-guided genome editing for target gene mutations in wheat. G3 (Bethesda). Dec. 9, 2013;3(12):2233-8. doi:10.1534/g3.113.008847.
Walther et al., Genetic prognostic and predictive markers in colorectal cancer. Nat Rev Cancer. Jul. 2009;9(7):489-99. doi: 10.1038/nrc2645. Epub Jun. 18, 2009. Review. Erratum in: Nat Rev Cancer. Apr. 2011;11(4):309.
Zang et al., Production of recombinant proteins in Chinese hamster ovary cells using a protein-free cell culture medium. Biotechnology (N Y). Apr. 1995;13(4):389-92.
Baruch et al., Enzyme activity—it's all about image. Trends Cell Biol. Jan. 2004;14(1):29-35.

* cited by examiner (From Pagliuca FW and Melton DA, *Development* (2013))

EXTENSIBLE RECOMBINASE CASCADES

RELATED APPLICATION

This application claims the benefit under 35 U.S.C. § 119(e) of U.S. provisional application No. 62/327,479, filed Apr. 26, 2016, which is incorporated by reference herein in its entirety.

GOVERNMENT FUNDING

This invention was made with government funding support under Grant No. OD008435 awarded by the National Institutes of Health. The government has certain rights in this invention.

FIELD OF INVENTION

This invention related to methods and genetic constructs for sequential, multiplexed, and extensible genetic perturbations.

BACKGROUND

Conventional genetic tools comprising inducible components are restricted in complexity due to the limited number of inducible systems and inducer molecules. Furthermore, such tools only provide a limited perspective of gene regulation and lack appreciation for the spatiotemporal dynamics of gene regulation and how this translates to biological function in a cell.

SUMMARY OF INVENTION

Aspects of the present invention provide genetic constructs comprising a plurality of genetic perturbation cassettes, wherein the plurality of genetic perturbation cassettes comprises a first type of genetic perturbation cassette comprising a first nucleic acid encoding a first inducible recombinase the recombinase activity of which is induced by a first inducer, a first gene element, a first terminator, and a first pair of recombinase recognition sites flanking the first recombinase, the first gene element, and the first terminator, wherein the first recombinase is capable of binding to and cleaving the first nucleic acid at each recombinase recognition site of the first pair of recombination recognition sites; and a second type of genetic perturbation cassette comprising a second nucleic acid encoding a second inducible recombinase the recombinase activity of which is induced by a second inducer, a second gene element, a second terminator, and a second pair of recombinase recognition sites flanking the second recombinase, the second gene element, and the second terminator, wherein the second recombinase is capable of binding to and cleaving the second nucleic acid at each recombinase recognition site of the second pair of recombination recognition sites. In some embodiments, the plurality of genetic perturbation cassettes comprises one or more of the first type of genetic perturbation cassettes alternating with one or more of the second type of genetic perturbation cassettes.

In some embodiments, the genetic constructs further comprise a third type of genetic perturbation cassette comprising a third nucleic acid encoding a third inducible recombinase the recombinase activity of which is induced by a third inducer, a third gene element, a third terminator, and a third pair of recombinase recognition sites flanking the third recombinase, the third gene element, and the third terminator, wherein the third recombinase is capable of binding to and cleaving the third nucleic acid at each recombinase recognition site of the third pair of recombination recognition sites.

In some embodiments, the genetic constructs further comprise a promoter located upstream of the first type of genetic perturbation cassette. In some embodiments, the promoter is a cell-specific promoter or a cell state-specific promoter.

In some embodiments, a nucleic acid encoding the first gene element is located within the 3' untranslated region of a nucleic acid encoding the first inducible recombinase and/or a nucleic acid encoding the second gene element is located within the 3' untranslated region of a nucleic acid encoding the second inducible recombinase. In some embodiments, a nucleic acid encoding the first gene element is located within an intron of a nucleic acid encoding the first inducible recombinase and/or a nucleic acid encoding the second gene element is located within an intron of a nucleic acid encoding the second inducible recombinase. In some embodiments, the gene element is a nucleic acid encoding a protein, a RNA, a gRNA, a miRNA, or a shRNA.

In some embodiments, the first inducible recombinase and/or the second inducible recombinase is a tyrosine recombinase. In some embodiments, the first inducible recombinase and/or the second inducible recombinase is a serine recombinase. In some embodiments, the first inducible recombinase and/or the second inducible recombinase is a split recombinase. In some embodiments, the split recombinase comprises a first portion and a second portion of the split recombinase.

In some embodiments, one or more of the genetic perturbation cassettes of the plurality of genetic perturbation cassettes comprises one or more ribozyme sequence. In some embodiments, each of the genetic perturbation cassettes of the plurality of genetic perturbation cassettes comprises one or more ribozyme sequence. In some embodiments, one or more of the genetic perturbation cassettes of the plurality of genetic perturbation cassettes comprises one or more ribonuclease recognition sequences. In some embodiments, each of the genetic perturbation cassettes of the plurality of genetic perturbation cassettes comprises one or more ribonuclease recognition sequences. In some embodiments, the one or more ribonuclease recognition sequences are Cas6/Csy4 recognition sequences.

In some embodiments, one or more of the genetic perturbation cassettes of the plurality of genetic perturbation cassettes comprises one or more self-cleaving peptide sequences. In some embodiments, the one or more self-cleaving peptide sequences is a P2A sequence.

In some embodiments, any of the inducers is a small molecule inducer. In some embodiments, the small molecule inducer is a hormone. In some embodiments, the hormone is gibberellin (GIB) or abscisic acid (ABA). In some embodiments, the small molecule inducer is an antibiotic. In some embodiments, the antibiotic is trimethoprim. In some embodiments, the small molecule inducer is a synthetic ligand. In some embodiments, the synthetic ligand is 4-hydroxytamoxifen or Shield-1 ligand.

Aspects of the present invention provide vectors comprising any of the genetic constructs described herein. Other aspects of the present invention provide recombinant cells comprising any of the genetic constructs described herein or vectors comprising any of the genetic constructs described herein. In some embodiments, the recombinant cell further comprises a Cas6/Csy4 ribonuclease. In some embodiments, the recombinant cell further comprises a Cas9 endonuclease.

In some embodiments, the recombinant cell is a bacterial cell, a fungal cell, a yeast cell, an insect cell, a plant cell, an animal cell, or a human cell. In some embodiments, the recombinant cell is a stem cell. In some embodiments, the stem cell is an embryonic stem cell or an induced pluripotent stem cell (iPS).

Also provided herein are transgenic organisms comprising any of the recombinant cells described herein. In some embodiments, the transgenic organism is a transgenic non-human organism.

Other aspects of the present invention provide methods for assessing gene expression in a cell, comprising (i) providing to a cell a genetic construct comprising a plurality of genetic perturbation cassettes, wherein the plurality of genetic perturbation cassettes comprises (a) a first type of genetic perturbation cassette comprising a nucleic acid encoding a first inducible recombinase the recombinase activity of which is induced by a first inducer, a first gene element, a first terminator, and a first pair of recombinase recognition sites flanking the first recombinase, the first gene element, and the first terminator, wherein the first recombinase is capable of binding to and cleaving the first nucleic acid at each recombinase recognition site of the first pair of recombination recognition sites; and (b) a second type of genetic perturbation cassette comprising a second nucleic acid encoding a second inducible recombinase the recombinase activity of which is induced by a second inducer, a second gene element, a second terminator, and a second pair of recombinase recognition sites flanking the second recombinase, the second gene element, and the second terminator, wherein the second recombinase is capable of binding to and cleaving the second nucleic acid at each recombinase recognition site of the second pair of recombination recognition sites; (ii) incubating the cell of (i) under conditions in which a first genetic perturbation cassette is expressed and the gene element is cleaved from the nucleic acid; and (iii) assessing an output of one or more targets of the gene element.

In some embodiments, the plurality of genetic perturbation cassettes further comprises a third type of genetic perturbation cassette comprising a third nucleic acid encoding a third inducible recombinase the recombinase activity of which is induced by a third inducer, a third gene element, a third terminator, and a third pair of recombinase recognition sites flanking the third recombinase, the third gene element, and the third terminator, wherein the third recombinase is capable of binding to and cleaving the third nucleic acid at each recombinase recognition site of the third pair of recombination recognition sites.

In some embodiments, the output of one or more targets of the first, second, and/or third gene element involves assessing expression of the one or more targets.

These and other aspects of the invention, as well as various embodiments thereof, will become more apparent in reference to the drawings and detailed description of the invention.

Each of the limitations of the invention can encompass various embodiments of the invention. It is, therefore, anticipated that each of the limitations of the invention involving any one element or combination of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. For purposes of clarity, not every component may be labeled in every drawing. In the drawings:

FIG. 1A shows a spatiotemporally regulated cascade including a cell-type-specific promoter ($P_{specific}$), and three Genetic Perturbation Cassettes (GPCs), each consisting of an inducible recombinase (rec), a gRNA that can modulate downstream targets in multiplexed fashion when used with CRISPR-Cas transcription factors, and a transcriptional terminator (Term), all flanked between the cognate recombinase recognition sites (R1). Recombinase 1 (Rec1), including gRNA1, is expressed under control of $P_{specific}$. Inducer 1 activates Rec1 activity, which self-excises the first GPC using the corresponding recombinase sites (R1, shown by brackets). FIG. 1B shows expression of recombinase 2 (Rec2), including gRNA2. gRNA2 modulates downstream targets using CRISPR-Cas transcription factors. Inducer 2 activates Rec2 activity, which self-excises the second GPC using the corresponding recombinase sites (R2, shown by triangles). FIG. 1C shows expression of recombinase 3 (Rec3), including gRNA3. gRNA3 modulates downstream targets using CRISPR-Cas transcription factors. Inducer 1 activates Rec3 activity, which self-excises the third GPC using the corresponding recombinase sites (R3, shown by arrows).

FIG. 3A shows representative flow cytometry plot 96 hours after treatment with vehicle or drug. FIG. 3B shows a plot of the quantification of the excision efficiency of samples analyzed in FIG. 3A. Excision efficiency is calculated as (% BFP positive)/(% BFP or mCherry positive).

FIG. 4A shows a schematic illustration of the development of colorectal cancer from normal epithelium through sequential mutation of APC, KRS, p53, and Smad4 (adapted from Walther et al. Nat. Rev. Cancer. (2009)9(7): 489-99). FIG. 4B shows a schematic illustration of an extensible recombinase cascade including four genetic perturbation cassettes. The first genetic perturbation cassette encodes a recombinase (rec1) and gRNAs that lead to mutation of APC, flanked by recognition sequences for the recombinase, indicated by brackets. The second genetic perturbation cassette encodes a recombinase (rec2), flanked by recognition sequences for the recombinase, indicated by triangles. The third genetic perturbation cassette encodes a recombinase (rec3) and gRNAs that lead to mutation of Smad4, flanked by recognition sequences for the recombinase, indicated by arrows. The fourth genetic perturbation cassette encodes a recombinase (rec4) and gRNAs that lead to mutation of p53, flanked by recognition sequences for the recombinase, indicated by semi-circles.

FIG. 5A shows a schematic illustration of the cellular differentiation including a subset of transcription factors involved in the process (adapted from Pagliuca and Melton, *Development* (2013) 140(12): 2472-83). FIG. 5B shows a schematic illustration of an extensible recombinase cascade including four genetic perturbation cassettes. The first genetic perturbation cassette encodes a recombinase (rec1) and gRNAs that lead to differentiation of the cell into definitive endoderm, flanked by recognition sequences for the recombinase, indicated by brackets. The second genetic perturbation cassette encodes a recombinase (rec2) and gNRAs that lead to differentiation of the cell into pancreatic endoderm, flanked by recognition sequences for the recombinase, indicated by triangles. The third genetic perturbation cassette encodes a recombinase (rec3) and gRNAs that lead to differentiation of the cell into an endocrine progenitor, flanked by recognition sequences for the recombinase, indicated by arrows. The fourth genetic perturbation cassette encodes a recombinase (rec4) and gRNAs that lead to differentiation of the cell into a pancreatic beta cell, flanked by recognition sequences for the recombinase, indicated by semi-circles.

DETAILED DESCRIPTION

Conventional recombinant expression tools allow for the inducible control of multiple genes in parallel, for example using CRISPR-Cas transcription factors, and the induction of genetic changes in specific tissues or at defined times, for example using recombinase systems like the Cre-LoxP systems. The limited availability of inducible systems that can be used orthogonally relative to one another restricts the temporal complexity of genetic perturbations that can be achieved in a single cell. Provided herein are synthetic genetic constructs comprising a series of genetic perturbation cassettes, for scalable, sequential, and controllable perturbation of multiple sets of endogenous genes. Genetic perturbation constructs, such as those described herein, may be useful in evaluating spatiotemporal regulation of gene expression, for example how the spatiotemporal gene expression affects development and/or disease progression, such as in cancer models, metabolic diseases, and neurodegenerative diseases.

The design of the genetic constructs described herein allows for toggling (alternating) between two different inducers that induce at least two different recombinases, providing the potential for inducing a wide range of sequential and combinatorial gene programs. The genetic constructs described herein comprise at least two types of genetic perturbation cassettes each comprising a recombinase, a gene element, a terminator, and a pair of recombinase recognition sites. Such genetic constructs allow for the sequential and regulated control of perturbation of multiple sets of genes in a cell minimizing the number of inducers (e.g., using only two inducers). Furthermore, the presence of a terminator sequence at the 3' end of each of the genetic perturbation cassettes allows for expression of one recombinase at a time and available for activation by an inducer. As described herein, activation of the recombinase results in binding to the pair of recombinase recognition sites, excision of the corresponding genetic perturbation cassette, recombination of the DNA backbone allowing expression of the next genetic perturbation cassette.

Figure 1A:
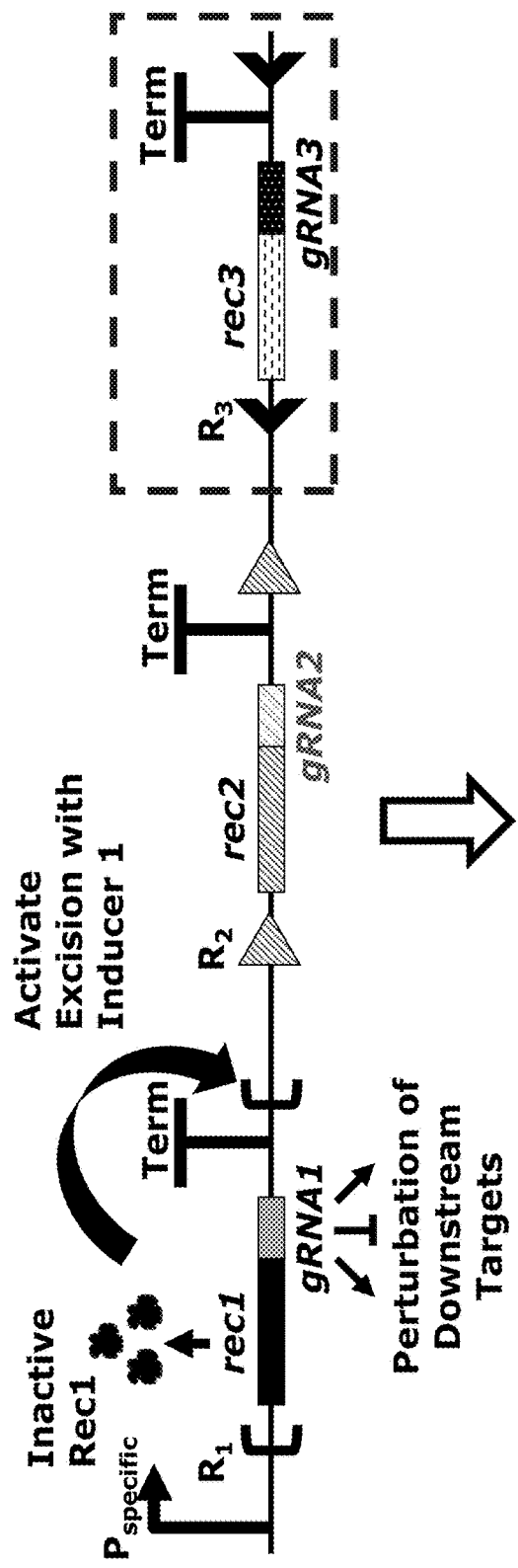
FIGS. 1A-1C show a schematic illustration of an example spatiotemporally regulated cascade for sequential, multiplexed, and extensible genetic perturbations in situ.

Aspects of the present disclosure relate to genetic constructs, vectors comprising genetic constructs, recombinant cells encoding genetic constructs, and methods of using said genetic constructs. As used herein, a "genetic construct" refers to one or more DNA element(s) comprising two or more genetic perturbation cassettes. The term "genetic perturbation cassette" (GPC) refers to a nucleic acid sequence which comprises an inducible recombinase, a gene element, a terminator, and a pair of recombinase recognition sites. The genetic construct may also encode a promoter upstream of the first genetic perturbation cassette that allows expression of the genetic perturbation cassettes in a sequential manner. The genetic constructs described herein allow for toggling (alternating) between two inducers by alternating the order of the types of genetic perturbation cassettes within the genetic construct. For example, as shown in FIG. 1A, the first GPC (the most 5' GPC) of the genetic construct may be a first type of GPC that is induced by a first inducer (Inducer 1), followed by a second GPC that is of a second type of GPC and induced by a second inducer (Inducer 2), followed by a third GPC that is of the first type of GPC and is induced by the first inducer (Inducer 1). In some embodiments, a first inducer can be used to activate the recombinases 1, 3, 5, and so forth, whereas the second inducer can be used to activate recombinases 2, 4, 6, and so forth. In some embodiments, the genetic construct contains at least 2, 3, 4, 5, 6, 7, 8, 9, 10 or more genetic perturbation cassettes.

In some embodiments, any of the genetic constructs described herein may comprise a third type of genetic perturbation cassette that contains an inducible recombinase, a gene element, a terminator, and a pair of recombinase recognition sites. In some embodiments, the recombinase of the third type of genetic perturbation cassette is induced by an inducer that is different than the first and second inducers.

Aspects of the present disclosure provide inducible recombinases that when activate excise their corresponding genetic perturbation cassette from the genetic construct. Such a recombinase or cassette encoding such a recombinase that mediates its own excision may be referred to as a suicide recombinase or a suicide cassette.

As used herein, an "inducible recombinase" refers to an protein with recombinase activity (i.e., capable of catalyzing recombination of double-stranded DNA) that is inducible. The term "inducer" refers to a molecule or a signal that triggers or induces activation of the recombinase. In some embodiments, inducer of the recombinase activity is the presence and/or binding of a small molecule. In some embodiments, the inducer is the absence of or removal of a small molecule. Alternatively or in addition, the activity of the recombinase is induced by a signal within the host cell. In some embodiments, the inducer promotes activation of the recombinase activity by inducing protein dimerization. In some embodiments, the inducer promotes activation of the recombinase activity by protein translocation.

Any inducer known in the art may be compatible with the genetic perturbation cassettes described herein. Examples of inducers include, without limitation, methanol, IPTG, copper, antibiotics such as tetracycline or trimethoprim, carbon source, light, and hormones. In some embodiments, any of the inducers described herein may be small molecules, such as a small molecule inhibitor or small molecule activator. As used herein, a "small molecule" refers to a compound having a low molecule weight (i.e., less than 900 Daltons). In some embodiments, the inducer is a hormone. Examples of hormone inducers include gibberellin (GIB) and abscisic acid (ABA). In some embodiments, the inducer is a exogenous molecule. In some embodiments, the inducer is an antibiotic. In some embodiments, the inducer is an endogenous molecule that is produced by the cell, for example during specific developmental stage.

In some embodiments, the inducer is a synthetic ligand. As used herein, the term "synthetic ligand" refers to any non-naturally-occurring ligand that can induce or activate a recombinase, directly or indirectly. In some embodiments, the synthetic ligand interacts with (binds to) the recombinase and activates its enzymatic activity. In some embodiments, the synthetic ligand interacts with a binding domain, or portion thereof, to activate the enzymatic activity of the recombinase. In some embodiments, the synthetic ligand is 4-hydroxytamoxifen. In some embodiments, the synthetic ligand is Shield-1 ligand.

The concentration of the inducer to regulate activity of the recombinase will depend on factors such as any of the components of the inducible system and the level of recombinase activity desired. In some embodiments, the concentration of the inducer is between 0.001-50 µM, 0.05-10 µM, 0.01-5 µM, 0.05-1 µM, or 0.1-1 µM. In some embodiments, the concentration of the inducer is at least 0.01 µM, 0.02 µM, 0.03 µM, 0.04 µM, 0.05 µM, 0.06 µM, 0.07 µM, 0.08 µM, 0.09 µM, 0.1 µM. 0.15 µM, 0.2 µM, 0.3 µM, 0.4 25 µM, 0.5 µM, 0.6 µM, 0.7 µM, 0.8 µM, 0.9 µM, 1.0 µM, 1.1 µM, 1.2 µM, 1.3 µM, 1.4 µM, 1.5 µM or more.

It will be appreciated that some recombinases may need one or more additional cofactors and/or accessory proteins to mediate recombination of the genetic construct. In some embodiments, the inducible recombinase is obtained or derived from a bacterial recombinase, fungal recombinase, yeast recombinase, or bacteriophage recombinase. A variety of recombinase combinations can be used in the genetic constructs described herein.

In general, recombinases may be classified as tyrosine recombinases or serine recombinase based on a conserved nucleophilic amino acid residue of the protein. In some embodiments, any one or more of the inducible recombinases may be a tyrosine recombinase. Examples of tyrosine recombinases known in the art include Cre recombinase, Flp recombinase, XerC recombinase, XerD recombinase, Lambda integrase, HP1 integrase, or a derivative or variant thereof. In some embodiments, any one or more of the inducible recombinases may be a serine recombinase. Examples of serine recombinases known in the art include γ6, ParA, Tn3, Gin, φC31, BxbI, and R4. The genetic constructs described herein may be comprised of tyrosine recombinases, serine recombinases, or a combination of both tyrosine recombinases and serine recombinases. Additional examples of recombinases for use in the genetic constructs described herein include, without limitation, KD, B2, B3, R, and Dre recombinases, and large serine-type phage integrases.

Also within the scope of the present disclosure are derivatives or variants of recombinases in which one or more mutations are made in the nucleic acid sequence encoding the recombinase. Such mutations, including deletions, insertions, and/or substitution mutations, may be made, for example, to alter the activity of the recombinase, alter the mechanism by which activity of the recombinase is induced, and/or improve expression of the recombinase. In some embodiments, one or more mutations are made in the nucleic acid sequence encoding a recombinase to make the activity of the recombinase inducible. In some embodiments, the recombinase is a synthetic or artificial recombinase.

In some embodiments, the recombinase is fused to a binding domain that interacts with the inducer molecule thereby regulating the enzymatic activity of the recombinase.

In some embodiments, the fusion of an inducer molecule binding domain with the recombinase allows for regulation of the stability of the recombinase by the presence of the inducer. Examples of inducers that stabilize the recombinase thereby increasing the recombinase activity include, without limitation, 4-hydroxytamoxifen, Shield-1 ligand, and trimethoprim.

The binding domain for 4-hydroxytamoxifen is $ER^{T2}$, which is a point mutant of estrogen receptor ligand binding domain. In some embodiments, $ER^{T2}$, or a portion thereof, is fused to a recombinase or portion of a recombinase, such as a portion of a recombinase protein that has recombinase activity or an N-terminal or C-terminal portion of a split recombinase. The binding domain for Shield-1 is a destabilization domain (DD), which is a point mutant of a FKBP12 domain. In some embodiments, the DD, or a portion thereof, is fused to a recombinase or portion of a recombinase. The binding domain for trimethoprim is point mutant of dihydrofolate reductase from *E. coli*. In some embodiments, a trimethoprim binding domain, or portion thereof, is fused to a recombinase or a portion of a recombinase.

In some embodiments, the inducer binding domain is fused to the N-terminus of the full length recombinase. In some embodiments, the inducer binding domain is fused to the C-terminus of the full length recombinase.

Also within the scope of the present invention are split recombinases. In general, split recombinases are recombinases that have been expressed as two or more separate portions of the enzyme. For example, a recombinase may be expressed as two or more (e.g., 2, 3, 4 or more) portions. In some embodiments, each of the separate portions of the recombinase are each fused to a portion of a binding domain (e.g., an inducer binding domain). In some embodiments, interaction of the portions of the binding domain with the inducer results in interaction of the portions of the recombinase (e.g., dimerization) to reconstitute the enzymatic activity, thereby regulating the activity of the recombinase. Any recombinase known in the art may be used in the genetic perturbation cassettes described herein as a split recombinase.

In some embodiments, the split recombinase is expressed as an N-terminal portion and a C-terminal portion of the recombinase. The term "N-terminal portion" is used herein to refer to a portion of the recombinase extending from the first amino acid residue of the protein, the N-terminus. In some embodiments, the N-terminal portion is about 5%, 10%, 15%, 20%, 25%, 30%, 35%, 40%, 45%, 50%, 55%, 60%, 65%, 70%, 75%, 80%, 85%, 90%, 95% or more of the full length recombinase. As also used herein, the term "C-terminal portion" refers to a portion of the recombinase that includes the last amino acid residue of the protein, the C-terminus. In some embodiments, the C-terminal portion is about 5%, 10%, 15%, 20%, 25%, 30%, 35%, 40%, 45%, 50%, 55%, 60%, 65%, 70%, 75%, 80%, 85%, 90%, 95% or more of the full length recombinase.

In some embodiments, the recombinase is Cre recombinase and is expressed as a split recombinase comprising an N-terminal portion and a C-terminal portion. In some embodiments, the recombinase is a split Cre recombinase and comprises an N-terminal portion that is 75% of the full length Cre recombinase and a C-terminal portion that is 25% of the full length Cre recombinase.

In some embodiments, the recombinase is FlpO recombinase and is expressed as a split recombinase comprising an N-terminal portion and a C-terminal portion. In some embodiments, the recombinase is a split FlpO recombinase and comprises an N-terminal portion that is 95% of the full length FlpO recombinase and a C-terminal portion that is 5% of the full length FlpO recombinase.

In some embodiments, the recombinase is φC31 recombinase and is expressed as a split recombinase comprising an N-terminal portion and a C-terminal portion. In some embodiments, the split φC31 recombinase comprises an N-terminal portion that is 40% of the full length φC31 recombinase and a C-terminal portion that is 60% of the full length φC31 recombinase.

As described herein, each of the portions of a split recombinase may be fused to a portion of a binding domain (e.g., an inducer binding domain), such that interaction with the corresponding inducer allows for interaction between the portions of the recombinase. In some embodiments, the inducer binding domain may be separated into two portions, for example, an N-terminal portion and a C-terminal portion of the binding domain. In some embodiments, the N-terminal portion of the split recombinase may be fused to the N-terminal portion of the inducer binding domain. In some embodiments, the N-terminal portion of the split recombinase may be fused to the C-terminal portion of the inducer binding domain. In some embodiments, the C-terminal portion of the split recombinase may be fused to the C-terminal portion of the inducer binding domain. In some embodiments, the C-terminal portion of the split recombinase may be fused to the N-terminal portion of the inducer binding domain.

As used herein, the "N-terminal portion" in reference to the inducer binding domain means a portion of the inducer binding domain extending from the first amino acid residue of the domain, the N-terminus. In some embodiments, the N-terminal portion is about 5%, 10%, 15%, 20%, 25%, 30%, 35%, 40%, 45%, 50%, 55%, 60%, 65%, 70%, 75%, 80%, 85%, 90%, 95% or more of the full length binding domain. As also used herein, the term "C-terminal portion" in reference to the inducer binding domain means a portion of the inducer binding domain that includes the last amino acid residue of the domain, the C-terminus. In some embodiments, the C-terminal portion is about 5%, 10%, 15%, 20%, 25%, 30%, 35%, 40%, 45%, 50%, 55%, 60%, 65%, 70%, 75%, 80%, 85%, 90%, 95% or more of the full length binding domain.

Any binding domain that interacts with a corresponding inducer may be used in the constructs described herein. For example, in some embodiments, the inducer is gibberellin and the binding domain is a protein domain that interacts with gibberellin. In some embodiments, the inducer is gibberellin and the binding domains are Gibberellin Insensitive Dwarf1 (GID1), or a portion thereof that can bind to gibberellin, and Gibberellin Insensitive (GAI), or a portion thereof that can bind to gibberellin. In some embodiments, the inducer is abscisic acid and the binding domain is a protein domain that interacts with abscisic acid. In some embodiments, the inducer is abscisic acid and the binding domains are abscisic acid insensitive (ABI), or a portion thereof that can bind to abscisic acid, and PYL ABI receptor, or a portion thereof that can bind to abscisic acid.

In some embodiments, there may be a linker sequence between the portion of the split recombinase and the portion of the binding domain. As will be understood by one of skill in the art, linker sequences may be useful for allowing proper protein folding, enzymatic activity, and/or interaction with the ligand (inducer) and/or other portion of the split recombinase.

The genetic perturbation cassettes described herein each include a pair of recombinase recognition sites flanking the recombinase, gene element and promoter components of the genetic perturbation cassette. Upon activation of the recombinase, the recombinase is able to recognize and bind to its cognate recombinase recognition sites, leading to excision of the genetic material located between the recombinase recognition sites (e.g., the nucleic acid encoding the recombinase, gene element and terminator). Recombinase recognition sites are generally short (i.e., approximately 30-40 nucleotides) DNA sequences recognized by a cognate recombinase. The recombinase recognition site may include a palindromic sequence or a region that is palindromic.

Each pair of recombinase recognition sites of the genetic constructs described herein are distinct, such that activation of a recombinase leads to excision of the genetic perturbation cassette encoding that recombinase. For example, activation of the recombinase of the first genetic perturbation cassette of a genetic construct allows the recombinase to recognize and bind the cognate recombinase recognition sites flanking the first genetic perturbation cassette but not the recombinase recognition sites flanking other genetic perturbation cassettes (i.e., the second genetic perturbation cassette, the third genetic perturbation cassette, etc.).

A component or components of a genetic construct are said to be "flanked" by other genetic elements when the first component is located between and immediately adjacent to the other genetic elements. For example, FIG. 1A shows a schematic illustration of a genetic construct comprising three genetic perturbation cassettes, each of which are flanked by a pair of recombinase recognition sites, one 5' of each of the genetic perturbation cassettes and one 3' of each of the genetic perturbation cassettes.

Aspects of the disclosure relate to genetic perturbation cassettes comprising gene elements. As used herein, a "gene element" refers to any nucleic acid sequence for which expression and/or activity can be assessed. A gene element may include, without limitation, a protein coding sequence (a gene), an RNA, a microRNA, a shRNA, or a gRNA. It will be appreciated that each of the genetic perturbation cassettes may have the same or different type of gene element. For example, one genetic perturbation cassette of a plurality of genetic perturbation cassettes may contain a gRNA and one or more other genetic perturbation cassettes may contain another type of gene element (e.g., a gene, an RNA, a microRNA, or a shRNA). In some embodiments, each of the genetic perturbation cassette of a plurality of genetic perturbation cassettes may contain the same type of gene element, for example all of the genetic perturbation cassettes of the plurality may contain gRNAs.

In some embodiments, the gene element is a gene, such as a protein coding sequence. Any gene known in the art for which expression or activity of may be assessed to determine expression of the genetic perturbation cassette. In some embodiments, an activity of a product encoded by the gene may be assessed to determine expression of the genetic perturbation cassette. In some embodiments, the gene encodes a transcription factor, such as a transcription factor involved in a cell differentiation network controlling cell fate. In some embodiments, the gene encodes a reporter protein, such as an enzyme (e.g., galactosidase, fluorescence, luciferase, or alkaline phosphatase). In some embodiments, the gene encodes a fluorescent protein, such as red fluorescent protein (RFP), yellow fluorescent protein (YFP), blue fluorescent protein (BFP).

In some embodiments, the gene element is a microRNAs. The terms "microRNA" and "miRNA" may be used interchangeably throughout and refer to short, non-coding, single-stranded RNA molecules. miRNAs of the present disclosure may be naturally-occurring or synthetic (e.g., artificial). miRNAs usually induce gene silencing by binding to target sites found within the 3' UTR (untranslated region) of a targeted mRNA. This interaction prevents protein production by suppressing protein synthesis and/or by initiating mRNA degradation. Most target sites on the mRNA have only partial base complementarity with their corresponding microRNA, thus, individual microRNAs may target 100 different mRNAs, or more. Further, individual mRNAs may contain multiple binding sites for different miRNAs, resulting in a complex regulatory network. In some embodiments, a miRNA is 10 to 50 nucleotides in length. For example, a miRNA may be 10 to 40, 10 to 30, 10 to 20, 20 to 50, 20 to 40 or 20 to 30 nucleotides in length. In some embodiments, a miRNA is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In some embodiments, a miRNA is 22 nucleotides in length.

In some embodiments, the gene element is a shRNAs. In general, shRNAs are short RNA molecules forming or capable of forming a hairpin structure. shRNAs of the present disclosure may be naturally-occurring or synthetic (e.g., artificial). Binding of a shRNA to a target mRNA typically results in degradation of the mRNA. In some embodiments, a shRNA is 50 to 120 nucleotides in length. For example, a siRNA may be 50 to 100, 50 to 90, 50 to 80, 60 to 120, 60 to 100 or 70 to 90 nucleotides in length. In some embodiments, a siRNA 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101. 102, 103, 104, 105, 106, 107, 018, 109, 110, 111, 112, 113, 114, 115, 116, 117, 118, 119, or 120 nucleotides in length.

In some embodiments, the gene element is a gRNA. The terms "gRNA," "guide RNA" and "CRISPR guide sequence" may be used interchangeably throughout and refer to a nucleic acid comprising a sequence that determines the specificity of a Cas DNA binding protein of a CRISPR/Cas system. In some embodiments, the genetic perturbation cassette encoding a gRNA is for knocking out one or more genes with the CRISPR/Cas system, activating one or more genes with a CRISPR activation system; or inhibiting one or more genes with a CRISPR inhibition system. A gRNA is complementary to a target nucleic acid sequence in a host cell. The gRNA or portion thereof that is complementary to the target nucleic acid may be between 15-25 nucleotides, 18-22 nucleotides, or 19-21 nucleotides in length. In some embodiments, the gRNA sequence that is complementary to the target nucleic acid is 15, 16, 17, 18, 19, 20, 21, 22, 23, 24, or 25 nucleotides in length. In some embodiments, the gRNA sequence that is complementary to the target nucleic acid is 20 nucleotides in length. In addition to a sequence that is complementary to a target nucleic acid, in some embodiments, the gRNA also comprises a scaffold sequence. Expression of a gRNA encoding both a sequence complementary to a target nucleic acid and scaffold sequence has the dual function of both binding (hybridizing) to the target nucleic acid and recruiting the endonuclease to the target nucleic acid, which may result in site-specific CRISPR activity. In some embodiments, such a chimeric gRNA may be referred to as a single guide RNA (sgRNA).

As used herein, a "scaffold sequence," also referred to as a tracrRNA, refers to a nucleic acid sequence that recruits an endonuclease to a target nucleic acid bound (hybridized) to a complementary gRNA sequence. Any scaffold sequence that comprises at least one stem loop structure and recruits an endonuclease may be used in the genetic elements and vectors described herein. Exemplary scaffold sequences will be evident to one of skill in the art and can be found for example in Jinek, et al. *Science* (2012) 337(6096):816-821, Ran, et al. *Nature Protocols* (2013) 8:2281-2308, PCT Application No. WO2014/093694, and PCT Application No. WO2013/176772.

In some embodiments, the gRNA sequence does not comprise a scaffold sequence and a scaffold sequence is expressed as a separate transcript. In some embodiments, the genetic perturbation cassette also encodes a scaffold sequence. In such embodiments, the gRNA sequence further comprises an additional sequence that is complementary to a portion of the scaffold sequence and functions to bind (hybridize) the scaffold sequence and recruit the endonuclease to the target nucleic acid.

It will be appreciated that a gRNA sequence, or portion thereof, is complementary to a target nucleic acid in a host cell if the gRNA sequence is capable of hybridizing to the target nucleic acid. In some embodiments, the gRNA sequence is at least 50%, 55%, 60%, 65%, 70%, 75%, 80%, 85%, 90%, 95%, 96%, 97%, 98%, 99%, or at least 100% complementary to a target nucleic acid (see also U.S. Pat. No. 8,697,359, which is incorporated by reference for its teaching of complementarity of a gRNA sequence with a target polynucleotide sequence). It has been demonstrated that mismatches between a CRISPR guide sequence and the target nucleic acid near the 3' end of the target nucleic acid may abolish nuclease cleavage activity (Upadhyay, et al. *Genes Genome Genetics* (2013) 3(12):2233-2238). In some embodiments, the gRNA sequence is at least 50%, 55%, 60%, 65%, 70%, 75%, 80%, 85%, 90%, 95%, 96%, 97%, 98%, 99%, or at least 100% complementary to the 3' end of the target nucleic acid (e.g., the last 5, 6, 7, 8, 9, or 10 nucleotides of the 3' end of the target nucleic acid).

The gRNA sequence may be obtained from any source known in the art. For example, the gRNA sequence may be any nucleic acid sequence of the indicated length present in the nucleic acid of a host cell (e.g., genomic nucleic acid and/or extra-genomic nucleic acid). In some embodiments, gRNA sequences may be designed and synthesized to target desired nucleic acids, such as nucleic acids encoding transcription factors, signaling proteins, transporters, etc.

In some embodiments, the gRNAs of the present disclosure have a length of 10 to 500 nucleotides. In some embodiments, a gRNA has a length of 10 to 20 nucleotides, 10 to 30 nucleotides, 10 to 40 nucleotides, 10 to 50 nucleotides, 10 to 60 nucleotides, 10 to 70 nucleotides, 10 to 80 nucleotides, 10 to 90 nucleotides, 10 to 100 nucleotides, 20 to 30 nucleotides, 20 to 40 nucleotides, 20 to 50 nucleotides, 20 to 60 nucleotides, 20 to 70 nucleotides, 20 to 80 nucleotides, 20 to 90 nucleotides, 20 to 100 nucleotides, 30 to 40 nucleotides, 30 to 50 nucleotides, 30 to 60 nucleotides, 30 to 70 nucleotides, 30 to 80 nucleotides, 30 to 90 nucleotides, 30 to 100 nucleotides, 40 to 50 nucleotides, 40 to 60 nucleotides, 40 to 70 nucleotides, 40 to 80 nucleotides, 40 to 90 nucleotides, 40 to 100 nucleotides, 50 to 60 nucleotides, 50 to 70 nucleotides, 50 to 80 nucleotides, 50 to 90 nucleotides or 50 to 100 nucleotides. In some embodiments, a gRNA has a length of 10 to 200 nucleotides, 10 to 250 nucleotides, 10 to 300 nucleotides, 10 to 350 nucleotides, 10 to 400 nucleotides or 10 to 450 nucleotides. In some embodiments, a gRNA has a length of more than 500 nucleotides. In some embodiments, a gRNA has a length of 10, 15, 20, 15, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 or more nucleotides.

The terms "target nucleic acid," "target site," and "target sequence" may be used interchangeably throughout and refer to any nucleic acid sequence in a host cell that may be targeted by the gRNA sequences described herein. The target site(s) may also be referred to as "downstream targets" of a gRNA. The target nucleic acid is flanked on the 3' side by a protospacer adjacent motif (PAM) that may interact with the endonuclease and be further involved in targeting the endonuclease activity to the target nucleic acid. It is generally thought that the PAM sequence flanking the target nucleic acid depends on the endonuclease and the source from which the endonuclease is derived. For example, for Cas9 endonucleases that are derived from *Streptococcus pyogenes*, the PAM sequence is NGG. For Cas9 endonucleases derived from *Staphylococcus aureus*, the PAM sequence is NNGRRT. For Cas9 endonucleases that are derived from *Neisseria meningitidis*, the PAM sequence is NNNNGATT. For Cas9 endonucleases derived from *Streptococcus thermophilus*, the PAM sequence is NNAGAA. For Cas9 endonuclease derived from *Treponema denticola*, the PAM sequence is NAAAAC. For a Cpf 1 nuclease, the PAM sequence is TTN.

In other embodiments, the recombinase and the gene element are transcribed as separate mRNA transcripts. In some embodiments, the recombinase and the gene element of a genetic perturbation cassette are transcribed as a single mRNA transcript. In some embodiments, the nucleic acid encoding the gene element is within the nucleic acid encoding the recombinase. As used herein, a nucleic acid sequence is considered within another nucleic acid sequence if the first nucleic acid sequence is inserted between two nucleotides of the second nucleic acid sequence, or if the first nucleic acid sequence replaces a stretch of contiguous nucleotides of the second nucleic acid sequence. In some embodiments, the nucleic acid encoding the gene element is within a non-protein coding portion of the recombinase, such as an untranslated region of the recombinase. In some embodiments, the nucleic acid encoding the gene element is within the 3'UTR sequence of the recombinase. In some embodiments, the gene element is encoded within an intron of the recombinase nucleic acid sequence. Methods for encoding and removing a gene element from within a portion of another gene, such as a recombinase described herein, are known in the art. See, e.g., Nissim et al. *Mol. Cell* (2014) 54: 1-13.

In some embodiments, the nucleic acid encoding the gene element is within the 3'UTR sequence of the recombinase and the gene element is removed from the sequence of the recombinase after transcription. In some embodiments, the gene element of the present disclosure is flanked by ribonuclease recognition sites. A ribonuclease (abbreviated as RNase) is a nuclease that catalyzes the hydrolysis of RNA. A ribonuclease may be an endoribonuclease or an exoribonuclease. An endoribonuclease cleaves either single-stranded or double-stranded RNA. An exoribonuclease degrades RNA by removing terminal nucleotides from either the 5' end or the 3' end of the RNA. In some embodiments, gene element of the present disclosure, such as a gRNA, is flanked by Csy ribonuclease recognition sites (e.g., Csy4 ribonuclease recognition sites). Csy4 is an endoribonuclease that recognizes a particular RNA sequence, cleaves the RNA, and remains bound to the upstream fragment. In some embodiments, a Csy ribonuclease (e.g., Csy4 ribonuclease) is used to release the gene element from a nucleic acid transcript. Thus, in some embodiments, cells comprising any of the genetic constructs described herein including a gene element flanked by Csy4 or other Cas6 ribonuclease recognition sites also contain a nucleic acid encoding a Csy4 or other Cas6 ribonuclease. In some embodiments, the activity of a Csy4 or other Cas6 ribonuclease is inducible or regulatable by the presence of one or more inducer molecules, such that the gene element flanked by ribonuclease recognition sites is only cleaved when the ribonuclease is in the presence of an inducer. Use of Csy4 or other Cas6 ribonucleases for the excision of gene elements is known in the art, see, e.g., PCT Application No. WO 2015/153940.

In some embodiments, the cell may stably express, or be modified to stably express, a Csy4 or other Cas6 ribonuclease. In some embodiments, a Csy ribonuclease (e.g., Csy4 ribonuclease) is from *Pseudomonas aeruginosa*, *Staphylococcus epidermidis*, *Pyrococcus furiosus* or *Sulfolobus solfataricus*. Other ribonucleases and ribonuclease recognitions sites are contemplated herein (see, e.g., Mojica, F. J. M. et al., CRISPR-Cas Systems, RNA-mediated Adaptive Immunity in Bacteria and Archaea, Barrangou, Rodolphe, van der Oost, John (Eds.), 2013, ISBN 978-3-642-34657-6, of which the subject matter relating to ribonucleases/recognition sites is incorporated by reference herein).

In some embodiments, a ribonuclease recognition site (e.g., Csy4 ribonuclease recognition site) is 10 to 50 nucleotides in length. For example, a Csy ribonuclease recognition site may be 10 to 40, 10 to 30, 10 to 20, 20 to 50, 20 to 40 or 20 to 30 nucleotides in length. In some embodiments, a Csy ribonuclease recognition site is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In some embodiments, a Csy ribonuclease recognition site (e.g., Csy4 ribonuclease recognition site) is 28 nucleotides in length. In some embodiments, the nucleotide sequence encoding a ribonuclease recognition site comprises SEQ ID NO: 1 (GT-TCACTGCCGTATAGGCAGCTAAGAAA). Csy homologs are also contemplated herein (see, e.g., Mojica, F. J. M. et al., CRISPR-Cas Systems, RNA-mediated Adaptive Immunity in Bacteria and Archaea, Barrangou, Rodolphe, van der Oost, John (Eds.), 2013, ISBN 978-3-642-34657-6, of which the subject matter relating to ribonucleases/recognition sites is incorporated by reference herein).

Some aspects of the present disclosure relate to genetic perturbation cassettes that include a sequence encoding a gene element flanked by ribozymes. Ribozymes are RNA molecules that are capable of catalyzing specific biochemical reactions, similar to the action of protein enzymes. Cis-acting ribozymes are typically self-forming and capable of self-cleaving. Cis-acting ribozymes can mediate functional expression of a gene element, such as a gRNA, a shRNA, or a microRNA from RNA pol II promoters. Trans-acting ribozymes, by comparison, do not perform self-cleavage. Self-cleavage refers to the process of intramolecular catalysis in which the RNA molecule containing the ribozyme is itself cleaved. Examples of cis-acting ribozymes for use in accordance with the present disclosure include, without limitation, hammerhead (HH) ribozyme and Hepatitis delta virus (HDV) ribozyme. Examples of trans-acting ribozymes for use in accordance with the present disclosure include, without limitation, natural and artificial versions of the hairpin ribozymes found in the satellite RNA of tobacco ringspot virus (sTRSV), chicory yellow mottle virus (sCYMV) and arabis mosaic virus (sARMV). In some embodiments, the activity of the ribozyme is constitutive.

Some aspects of the present disclosure relate to genetic perturbation cassettes comprising a nucleic acid encoding a recombinase that includes a 3' RNA stabilizing sequence such as, for example, an RNA sequence that forms a triple helix structure (or "triplex"). In some embodiments, the nucleic acid sequence encoding the gene element is present within the sequence of the recombinase, such as the 3'UTR of the recombinase. In such embodiments, excision of the gene element from the transcript may result in a mRNA encoding a recombinase lacking a poly-(A) tail. In some embodiments, excision of the gene element from the transcript reduces the stability of the transcript encoding the recombinase. A 3' RNA stabilizing sequence is a sequence added to the 3' end of a nucleic acid sequence encoding a product to complement for the lack of a poly-(A) tail. Thus, 3' RNA stabilizing sequences, such as those that form triple helix structures, in some embodiments, enable efficient translation of mRNA lacking a poly-(A) tail. A triple helical structure is a secondary or tertiary RNA structure formed, for example, by adenine- and uridine-rich motifs. In some embodiments, a 3' RNA stabilizing sequence is from a 3' untranslated region (UTR) of a nucleic acid.

In some embodiments, the genetic perturbation cassette contains a self-cleaving peptide, such as a 2A peptide (P2A). In general, 2A peptides are approximately 18-22 amino acids in length and allow for the production of multiple proteins from a single messenger RNA (mRNA). In some embodiments, the 2A peptide is the T2A peptide (EGRG-SLLTCGDVEENPGP (SEQ ID NO: 2)), P2A (ATNF-SLLKQAGDVEENPGP (SEQ ID NO: 3)), E2A (QCT-NYALLKLAGDVESNPGP (SEQ ID NO: 4)), or F2A (VKQTLNFDLLKLAGDVESNPGP (SEQ ID NO: 5)). In some embodiments, the nucleotide sequence encoding a recombinase may be separated from the nucleotide sequence encoding a gene element by a nucleotide sequence encoding a 2A peptide. In some embodiments, the nucleotide sequence encoding a first portion of a split recombinase may be separated from the nucleotide sequence encoding a second portion of split recombinase by a nucleotide sequence encoding a 2A peptide. Each of the genetic perturbation constructs further comprise a terminator sequence. As used herein a "terminator" sequence refers to a nucleic acid sequence that signals a RNA polymerase to stop transcribing the DNA. The terminator may also trigger release of the newly transcribed mRNA molecule from the transcription machinery and/or dissociation of the RNA polymerase from the DNA. It will be appreciated that selection of an appropriate terminator will depend, for example, on the cell or cell type in which the genetic constructs are intended to be used. Each of the genetic perturbation cassettes described herein comprise a terminator sequence at the 3' end of the cassette, allowing for transcription of only the genetic perturbation cassette most proximate to the promoter at a time and production of one recombinase available for activation by an inducer at a time.

In some embodiments, the genetic constructs of the present disclosure comprise a promoter upstream of the genetic perturbation cassettes. The promoter sequence may be operably linked to the adjacent genetic perturbation cassette. A "promoter" is a control region of a nucleic acid at which initiation and rate of transcription of the remainder of a nucleic acid are controlled. A promoter may also contain sub-regions at which regulatory proteins and molecules may bind, such as RNA polymerase and other transcription factors. The promoter and/or any additional regulatory sequences said to be "operably" joined to another nucleic acid sequence, such as a genetic perturbation cassette, when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

Promoters may be constitutive, inducible, activatable, repressible, tissue-specific, cell-specific, cell-state specific, or any combination thereof. In some embodiments, the promoter is a constitutively active promoter, such as the promoter from the yeast phosphoglycerate kinase (pPGK). In some embodiments, the promoter is a tissue-specific promoter, meaning the promoter has activity in a specific type of tissue. In some embodiments, the promoter is a cell-specific promoter. Use of a tissue-specific or cell-specific promoter allows restriction of the activity of the genetic constructs within a defined set of cells. As used herein, a "cell-specific promoter" is a promoter sequence that has activity in a specific type of cell resulting in transcription of the adjacent genetic perturbation cassette. Examples of cell-specific promoters include, without limitation, promoter active in macrophages, lymphocytes, neutrophils, dendritic cells, endothelial cells, epithelial cells, muscle cells, neuronal cells, cells of a given tissue (e.g., kidney cells). Alternatively or in addition, the promoter may be cell-state specific promoter that is active when the cell is in a specific state, such as a developmental state, activation state, or disease state. Examples of promoters include, without limitation, a cell developmental stage-specific promoter, a cell state-specific promoter, a NFκB-specific promoter, and an engineered cell-specific promoter.

Also contemplated herein, in some embodiments, are RNA pol II and RNA pol III promoters. Promoters that direct accurate initiation of transcription by an RNA polymerase II are referred to as RNA pol II promoters. Examples of RNA pol II promoters for use in accordance with the present disclosure include, without limitation, human cytomegalovirus promoters, human ubiquitin promoters, human histone H2A1 promoters and human inflammatory chemokine CXCL 1 promoters. Other RNA pol II promoters are also contemplated herein. Promoters that direct accurate initiation of transcription by an RNA polymerase III are referred to as RNA pol III promoters. Examples of RNA pol III promoters for use in accordance with the present disclosure include, without limitation, a U6 promoter, a H1 promoter and promoters of transfer RNAs, 5S ribosomal RNA (rRNA), and the signal recognition particle 7SL RNA.

Any promoter known in the art may be used in the genetic constructs described herein and includes naturally occurring promoter sequences and synthetic or genetically modified promoter sequences. In some embodiments, the promoter is an artificial promoter.

In some embodiments, the genetic construct maybe targeted to and inserted into a DNA locus, referred to as a "landing pad" of the host cell. In some embodiments, the landing pad is in the genome of the host cell. In some embodiments, the landing pad is located in an extra-genomic DNA locus in the host cell, such as on a plasmid or a vector. In some embodiments, the genetic construct is present on a vector transduced into the host cell. In general, a landing pad is a region or within a region of nucleic acid that is considered to be a neutral site of the genome (or extra-genomic DNA), meaning insertion of the genetic construct would not be expected to have a an effect (negative or positive) on the host cell under conditions tested. Examples of landing pads or loci for insertion of the genetic constructs described herein include, without limitation, H11, AAVS1, CCR5, and ROSA26 loci. In some embodiments, the landing pad is on a human or mammalian artificial chromosome.

Also provided herein are recombinant cells comprising any of the genetic constructs described herein. Examples of cells include, without limitation, bacterial cells, algal cells, plant cells, insect cells, fungal cells, yeast cells, non-human mammalian cells, and human cells. In some embodiments, the cell is a bacterial cells.

In some embodiments, the cell is a eukaryotic cell, such as a mammalian cell. For example, in some embodiments, the genetic perturbation cassettes are expressed in human cells, primate cells (e.g., Vero cells), rat cells (e.g., GH3 cells, OC23 cells) or mouse cells (e.g., MC3T3 cells). There are a variety of human cell lines, including, without limitation, HEK cells, HeLa cells, cancer cells from the National Cancer Institute's 60 cancer cell lines (NCI60), DU145 (prostate cancer) cells, Lncap (prostate cancer) cells, MCF-7 (breast cancer) cells, MDA-MB-438 (breast cancer) cells, PC3 (prostate cancer) cells, T47D (breast cancer) cells, THP-1 (acute myeloid leukemia) cells, U87 (glioblastoma) cells, SHSY5Y human neuroblastoma cells (cloned from a myeloma) and Saos-2 (bone cancer) cells. In some embodiments, engineered constructs are expressed in human embryonic kidney (HEK) cells (e.g., HEK 293 or HEK 293T cells). In some embodiments, the genetic perturbation cassettes are expressed in stem cells (e.g., human stem cells) such as, for example, pluripotent stem cells (e.g., embryonic stem cells or induced pluripotent stem cells (iPSCs)).

In other embodiments, the cell is a fungal cell such as a yeast cell, e.g., *Saccharomyces* spp., *Schizosaccharomyces* spp., *Pichia* spp., *Phaffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. Preferably the yeast strain is a *S. cerevisiae* strain. Other examples of fungi include *Aspergillus* spp., *Penicillium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp.

In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp., and *Pantoea* spp. The bacterial cell can be a Gram-negative cell such as an *Escherichia coli* (*E. coli*) cell, or a Gram-positive cell such as a species of *Bacillus*.

Also within the scope of the present invention are transgenic organisms comprising cells containing the genetic constructs described herein. Routine methods known in the art may be used to generate transgenic organisms comprising cells containing the genetic constructs described herein. In some embodiments, the cell is in an multicellular organism, for example a plant or a mammal. In some embodiments, the transgenic organism is a transgenic non-human mammal. In some embodiments, the mammal is a rodent, such as a mouse or a rat.

In some embodiments, the cell in which the genetic construct is expressed may express one or more additional components, such as one or more CRISPR components, such as an endonuclease. In some embodiments, the recombinant cell naturally encodes a Cas9 enzyme. In some embodiments, the recombinant cell is engineered to encode a Cas9 enzyme or variant thereof. In some embodiments, the host cell also expresses an endonuclease, such as a Cas9 endonuclease. In some embodiments, the host cell expresses a Cas9 endonuclease derived from *Streptococcus pyogenes, Staphylococcus aureus, Neisseria meningitidis, Streptococcus thermophilus,* or *Treponema denticola*. In some embodiments, the nucleotide sequence encoding the Cas9 endonuclease may be codon optimized for expression in a host cell or organism. In some embodiments, the endonuclease is a Cas9 homolog or ortholog.

In some embodiments, the nucleotide sequence encoding the Cas9 endonuclease is further modified to alter the activity of the protein. In some embodiments, the Cas9 endonuclease is a catalytically inactive Cas9. For example, dCas9 contains mutations of catalytically active residues (D10 and H840) and does not have nuclease activity. Alternatively or in addition, the Cas9 endonuclease may be fused to another protein or portion thereof. In some embodiments, dCas9 is fused to a repressor domain, such as a KRAB domain. In some embodiments, such dCas9 fusion proteins are used with the constructs described herein for multiplexed gene repression (e.g., CRISPR interference (CRISPRi)). In some embodiments, dCas9 is fused to an activator domain, such as VP64 or VPR. CRISPR proteins comprising dCas9 fused to a transcription factor or domain therefrom are generally referred to as CRISPR-TF or CRISPR-transcription factors. Variant CRISPR-TF are also known in the art and may confer stronger transcriptional activation of a gene, as compared to a CRISPR-TF comprising, for example, dCas9-VP64. See, e.g., Chavez et al. *Nat. Methods* 5 (2015) 12: 326-328; Farzadfard et al. *ACS Synth. Biol*. (2015) 517: 583-588; Tanenbaum *Cell* (2014) 159: 635-646. In some embodiments, such dCas9 fusion proteins are used with the constructs described herein for multiplexed gene activation (e.g., CRISPR activation (CRISPRa)). See, e.g., Gilbert et al. *Cell* (2014) 159(3): 647-661. In some embodiments, dCas9 is fused to an epigenetic modulating domain, such as a histone demethylase domain or a histone acetyltransferase domain. In some embodiments, dCas9 is fused to a LSD1 or p300, or a portion thereof. In some embodiments, the dCas9 fusion is used for CRISPR-based epigenetic modulation. In some embodiments, dCas9 or Cas9 is fused to a Fok1 nuclease domain. In some embodiments, Cas9 or dCas9 fused to a Fok1 nuclease domain is used for multiplexed gene editing. In some embodiments, Cas9 or dCas9 is fused to a fluorescent protein (e.g., GFP, RFP, BFP, mCherry, etc.). In some embodiments, Cas9/dCas9 proteins fused to fluorescent proteins are used for multiplexed labeling and/or visualization of genomic loci.

Alternatively or in addition, the endonuclease is a Cpf1 nuclease. In some embodiments, the host cell expresses a Cpf1 nuclease derived from *Provetella* spp. or *Francisella* spp. In some embodiments, the nucleotide sequence encoding the Cpf1 nuclease may be codon optimized for expression in a host cell or organism.

Cells of the present disclosure, in some embodiments, are modified and may be referred to as recombinant cells. A modified cell or recombinant cell is a cell that contains an exogenous nucleic acid or a nucleic acid that does not occur in nature. In some embodiments, a recombinant cell contains an exogenous independently replicating nucleic acid (e.g., an genetic construct present on an episomal vector). In some embodiments, a recombinant cell is produced by introducing a foreign or exogenous nucleic acid into a cell. A nucleic acid may be introduced into a cell by conventional methods, such as, for example, electroporation, chemical transfection, viral transduction, phage transduction, fusion with bacterial protoplasts containing recombinant plasmids, or microinjection. In some embodiments, the genetic constructs are introduced into a cell on a plasmids or vectors. In some embodiments, the genetic constructs are introduced into a cell by a virus, such as lentiviruses or adenoviruses. Expressing the nucleic acid molecule may also be accomplished by integrating the nucleic acid molecule into the genome.

In some embodiments, genetic constructs as described herein are provided on a recombinant expression vector. As used herein, a "vector" may be any of a number of nucleic acids into which a desired sequence or sequences may be inserted, for example, by restriction digestion and ligation or by recombination for transport between different genetic environments or for expression in a host cell. Vectors are typically composed of DNA, although RNA vectors are also available. Vectors include, but are not limited to: plasmids, fosmids, phagemids, virus genomes, and artificial chromosomes. In some embodiments, the vector is a lentiviral vector. In some embodiments, each of the genes encoding the combination of two or three microRNAs are expressed on the same recombinant expression vector. In some embodiments, a gene encoding an endonuclease, such a CRISPR endonuclease (e.g., a Cas9 enzyme) is provided on a vector. In some embodiments, a gene encoding an endonuclease, such a CRISPR endonuclease, is provided on the same vector as the genetic constructs described herein. In some embodiments, a gene encoding an endonuclease, such a CRISPR endonuclease, is provided on a different vector than a vector containing the genetic constructs described herein.

Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., galactosidase, fluorescence, luciferase or alkaline phosphatase), and genes which visibly affect the phenotype of transformed or transfected cells, hosts, colonies or plaques (e.g., green fluorescent protein, red fluorescent protein). Preferred vectors are those capable of autonomous replication and expression of the structural gene products present in the DNA segments to which they are operably joined.

Also within the scope of the present disclosure are methods for assessing gene expression in a cell involving providing the cell with a genetic construct described herein and incubating the cell under conditions in which the first genetic perturbation cassette (the genetic perturbation cassette most proximate to the promoter) is expressed. In some embodiments, the conditions allow for the gene element to also be expressed. In embodiments in which the nucleic acid encoding the gene element is within the nucleic acid sequence encoding the recombinase, the cell is incubated under conditions in which the gene element is excised or cleaved from the recombinase transcript. For example, cells comprising a genetic construct of the present disclosure may be cultured (e.g., maintained in cell culture) using conventional cell culture methods. For example, cells may be grown and maintained at an appropriate temperature and gas mixture (e.g., 37° C., 5% CO2 for mammalian cells) in a cell incubator. In some embodiments, the cells may be incubated under specific conditions to induce a desired state of the cell, such as a development state, activation or disease state. Culture conditions may vary for each cell type. For example, cell growth media may vary in pH, glucose concentration, growth factors, and the presence of other nutrients. Growth factors used to supplement media are often derived from the serum of animal blood, such as fetal bovine serum (FBS), bovine calf serum, equine serum and/or porcine serum. In some embodiments, culture media used as provided herein may be commercially available and/or well-described (see, e.g., Birch J. R., R. G. Spier (Ed.) Encyclopedia of Cell Technology, Wiley. 411-424, 2000; Keen M. J. Cytotechnology 17:125-132, 1995; Zang, et al. Bio/Technology. 13: 389-392, 1995). In some embodiments, chemically defined media is used.

The temporal and sequential induction of each of the genetic perturbation cassettes may be evaluated by assessing the output of the gene element of each of the genetic perturbation cassettes. In some embodiments, the output of the gene element involves assessing the expression or activity of the gene element. Methods of assessing expression of a gene element will be evident to one of skill in the art and include, for example, qRT-PCR, microarray analysis, Northern blotting, and RNA-Seq. In some embodiments, gene element is a gene and expression of the gene is evaluated by quantifying the amount of the product of the gene. Alternatively or in addition, the activity of a gene element may be assessed, for example, by measuring the amount of a product that results from the activity of the gene element, and/or measuring the expression of a target, such as a target gene, of the gene element.

The invention is not limited in its application to the details of construction and the arrangement of components set forth in the description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The present invention is further illustrated by the following Examples, which in no way should be construed as further limiting. The entire contents of all of the references (including literature references, issued patents, published patent applications, and co-pending patent applications)

cited throughout this application are hereby expressly incorporated by reference, particularly for the teachings referenced herein.

EXAMPLES

Example 1

Figure 1B:
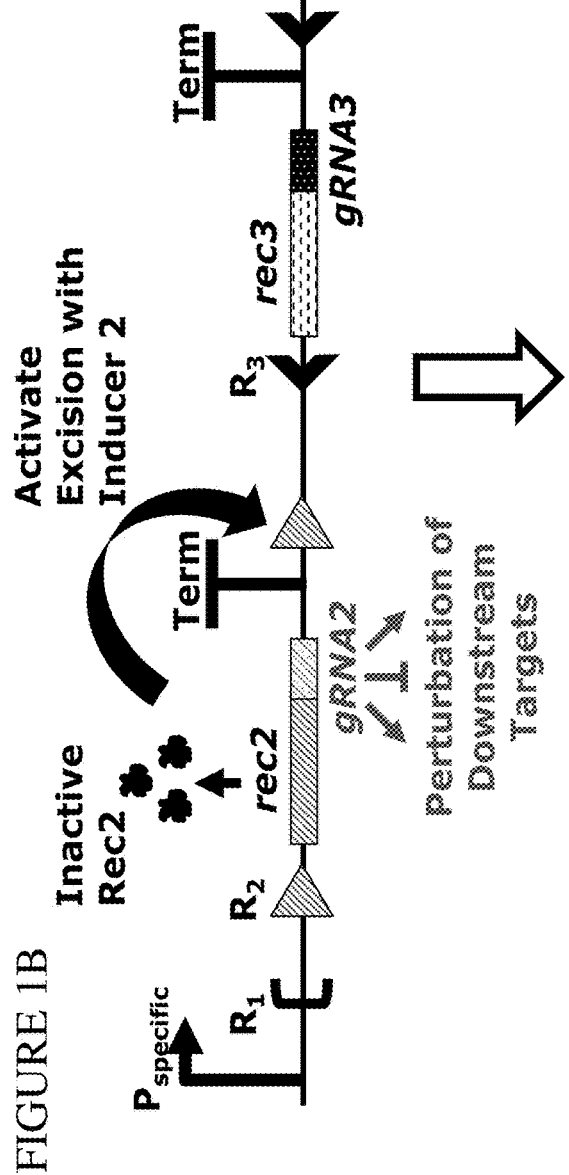
Figure 1C:
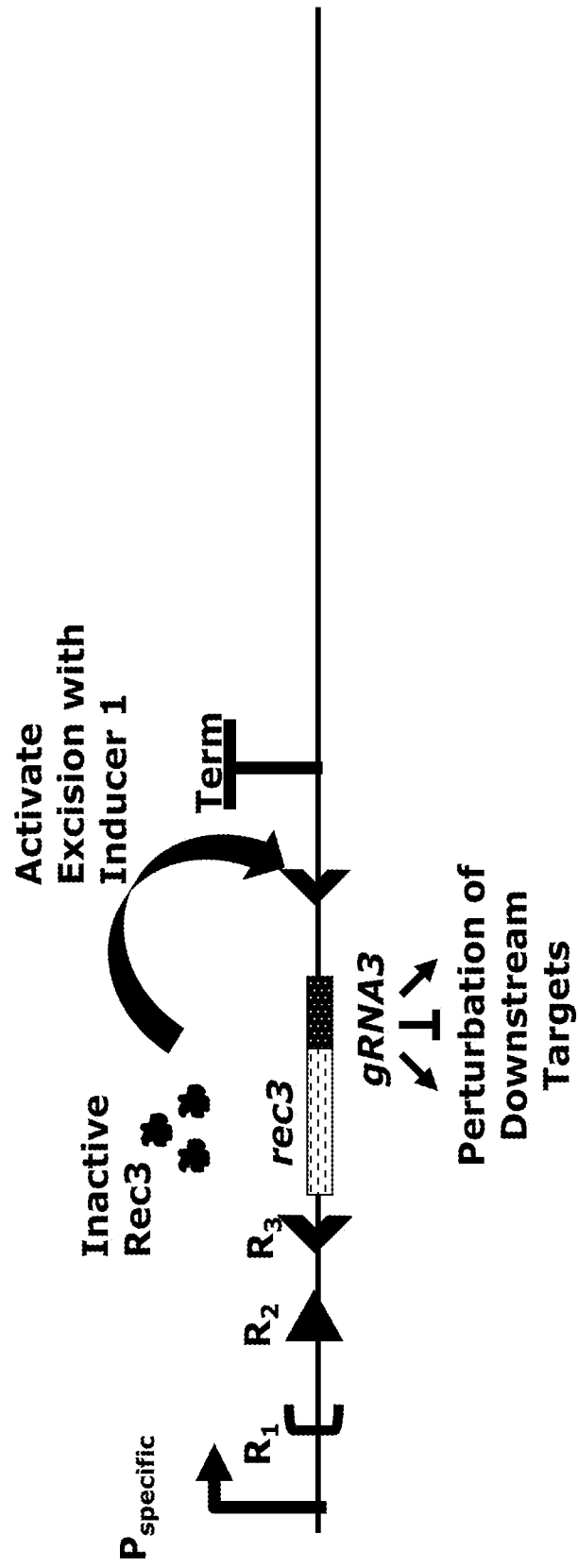

When present in a host cell, the first genetic perturbation cassette of the genetic construct is expressed under control of the promoter located upstream of the first genetic perturbation cassette of the construct (FIG. 1A). Expression of the genetic perturbation cassette allows for production of inactive recombinase (inactive Rec1) and the gRNA gene element which exerts an effect on downstream targets using CRISPR-Cas transcription factors. The inactive Rec1 is activated by Inducer 1 leading to self-excision of the first genetic perturbation cassette using the cognate recombinase sites (R1). Recombination with the pair of recombinase recognition sites (R1) allows for removal of the first genetic perturbation cassette and generation of a single R1 site. After removal of the first genetic perturbation cassette, the second genetic perturbation cassette is most proximate to the promoter, allowing for expression of the cassette and production of inactive recombinase 2 (Rec2) and gRNA2 (FIG. 1B). gRNA2 modulates downstream targets using CRISPR-Cas transcription factors. Inducer 2 activates Rec2 activity, which self-excises the second genetic perturbation cassette using the corresponding recombinase recognition sites (R2), resulting in the third genetic perturbation cassette becoming the genetic perturbation cassette most proximate to the promoter. The third genetic perturbation cassette is then expressed, producing inactive recombinase 3 (Rec3) and gRNA3 (FIG. 1C). gRNA3 modulates downstream targets using CRISPR-Cas transcription factors. Inducer 1 activates Rec3 activity, which self-excises the third GPC using the corresponding recombinase recognition sites (R3).

The perturbation (extent of activation or inhibition) of the downstream targets of the gRNAs is assessed to determine the timing and order of gene expression.

Example 2

Figure 2:
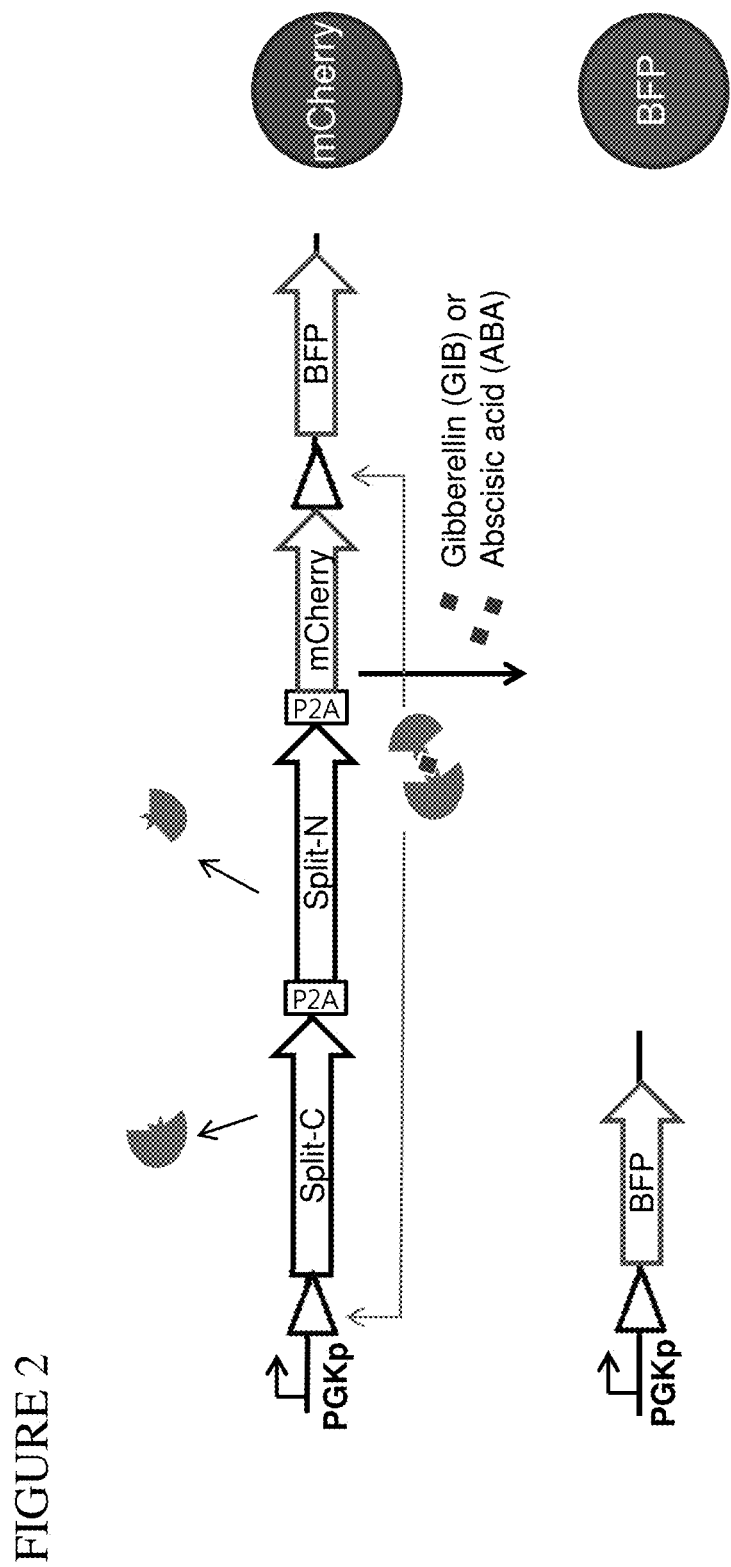
FIG. 2 shows a schematic illustration of an example cassette using a split recombinase. The N terminal- and C terminal-fragments of a recombinase (Split-N and Split-C) fused with binding domains for inducers gibberellin (GIB) or abscisic acid (ABA) and reporter fluorescent protein (mCherry) are flanked by recognition sequences of the recombinase, indicated by triangles. Addition of the inducer (GIB or ABA) induces dimerization and activation of the split-recombinase cassette to excise the genetic perturbation cassette and trigger expression of downstream gene (BFP).

Genetic perturbation cassettes were generated according to the general schematic presented in FIG. 2. The cassettes included a split recombinase expressed as a N-terminal portion (Split-N) and a C-terminal portion (Split-C) each of which was fused to a portion of a binding domain that specifically binds to an inducer (e.g., gibberellin (GIB) or abscisic acid (ABA). Specifically, the genetic perturbation cassette encoding a split Cre recombinase included an N-terminal portion that was 75% of the full length Cre recombinase and a C-terminal portion that was 25% of the full length Cre recombinase. The genetic perturbation cassette encoding a split FlpO recombinase included an N-terminal portion that was 95% of the FlpO recombinase and a C-terminal portion that was 5% of the full length FlpO recombinase.

In general, in the absence of the inducer, the portions of the split recombinase and mCherry are expressed. However, in the presence of the inducer, the portions of the split recombinase dimerize to reconstitute and activate the recombinase. Excision of the genetic perturbation cassette encoding mCherry allows for expression of the gene encoding blue fluorescent protein (BFP).

Figure 3A:
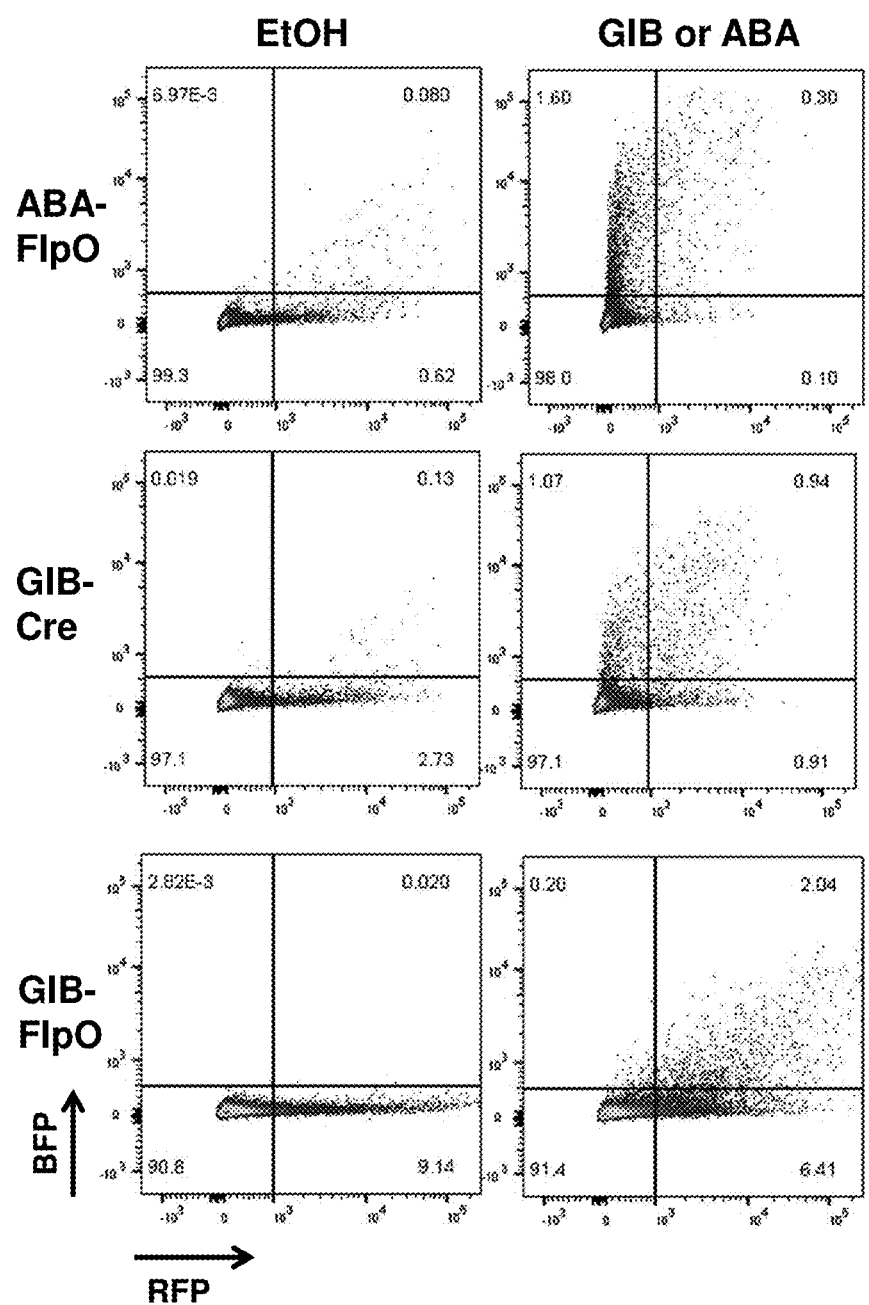
FIGS. 3A and 3B show validation of use of the genetic perturbation cassettes containing a split recombinase in cell culture. 293T cells were transiently transfected with the indicated split-recombinase cassette and treated with either vehicle (ethanol, EtOH) or an inducer (GIB or ABA). The recombinase-mediated excision of the cassette is assessed by BFP expression detected by flow cytometry (y-axis).

Three example genetic perturbation cassettes were produced: FlpO expressed as a split recombinase fused to a binding domain that interacts with ABA; Cre expressed as a split recombinase fused to a binding protein that interacts with GIB; and FlpO expressed as a split recombinase fused to a binding domain that interacts with GIB. 293 T cells were transiently transfected with the example genetic perturbation cassettes and treated with vehicle (ethanol) or the inducer (e.g., recombinase dimerizing drug: GIB or ABA). Expression of mCherry and BFP were assessed 96 hour after treatment by flow cytometric analysis (FIG. 3A). The data is also presented as the frequency of excision of the genetic perturbation cassette (leading to expression of BFP) calculated as the percent BFP cells/total cells (BFP position or mCherry positive) (FIG. 3B).

Figure 3B:
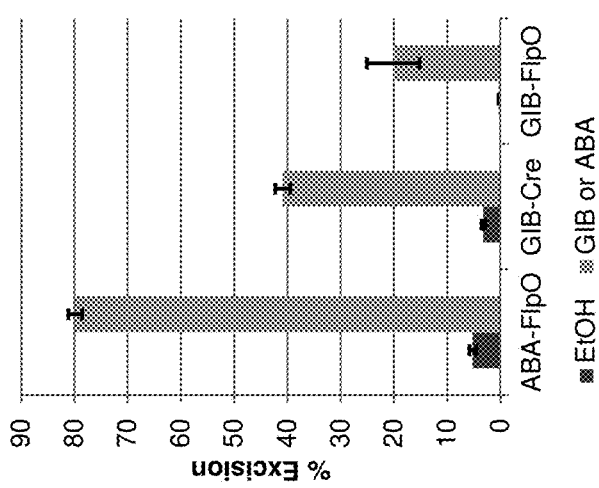

As shown in FIGS. 3A and 3B, treatment of the cells with the appropriate inducer resulted in an increase in excision of the genetic perturbation cassettes, leading to expression of the downstream gene, BFP.

Example 3

Figure 4A:
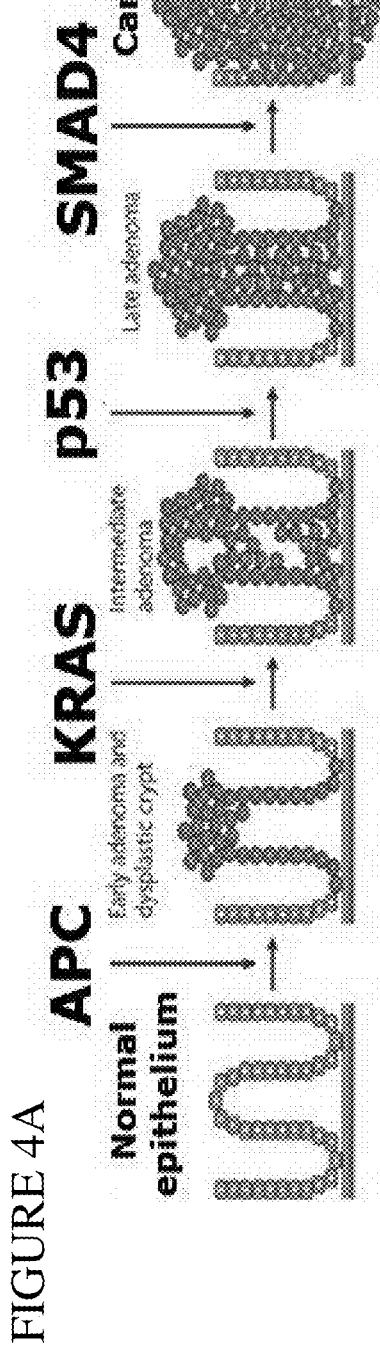
FIGS. 4A and 4B show an exemplary use of the extensible recombinase cascades described herein for establishing a tumorigenesis model.

The extensible recombinase cascades of genetic perturbation cassettes can be used to establish tumorigenesis models in which the causal mutations of a cancer are accumulated sequentially. For example, the four step tumorigenesis of colorectal cancer is defined by mutations of Adenomatous Polyposis Coli (APC), p53, KRAS and Smad4 as shown in FIG. 4A. This can be modeled using genetic perturbation cassettes, each of which encode a gRNA that can drive a tumorigenic mutation, such as APC, Smad4, or p53 mutations, or express a mutant oncogene, such as a KRAS mutant.

Figure 4B:
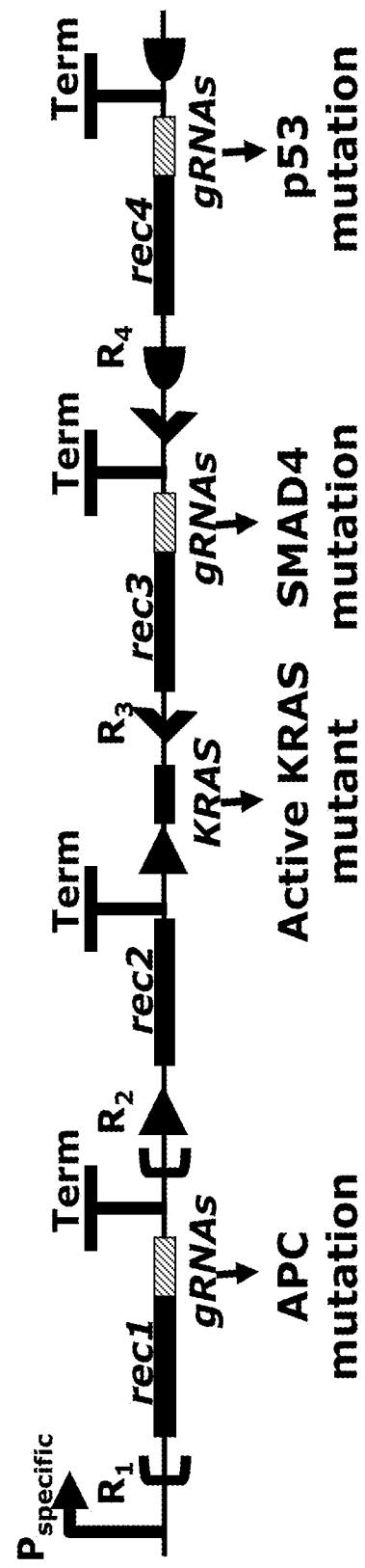

As shown in FIG. 4B, expression of the first genetic perturbation cassette leads to expression of one or more gRNAs that induce mutation of APC. Contact with a first inducer leads to excision of the first genetic perturbation cassette, allowing of expression of the second genetic perturbation cassette. Contact with a second inducer leads to excision of the second genetic perturbation cassette, allowing for expression of the active KRAS mutant as well as the third genetic perturbation cassette including one or more gRNAs that induce mutation of Smad4. Contact with a third inducer leads to the excision of the third perturbation cassette, allowing for expression of the fourth genetic perturbation cassette, including one or more gRNAs that induce mutation of p53. Development of the cancer (e.g., one or more cancer markers) can be assessed using methods known in the art prior to, during, and/or after contact with one or more inducers.

Example 4

Figure 5A:
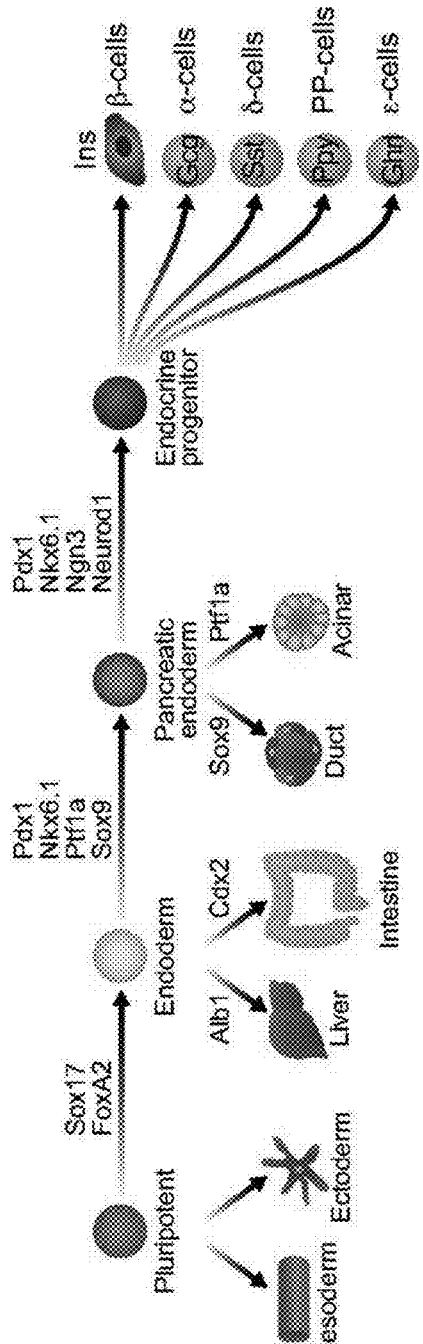
FIGS. 5A and 5B show an exemplary use of the extensible recombinase cascades described herein for differentiating progenitor cells into a specific cell type.

The extensible recombinase cascades of genetic perturbation cassettes can be used to establish efficient directed cellular differentiation. Sequential gene perturbation may mimic the natural developmental process of a specific cell type of therapeutic value. As shown in FIG. 5A, cellular differentiation involves the coordinated expression of a number of transcription factors, a subset of which are presented in the figure (from Pagliuca and Melton, *Development* (2013) 140(12): 2472-83).

Figure 5B:
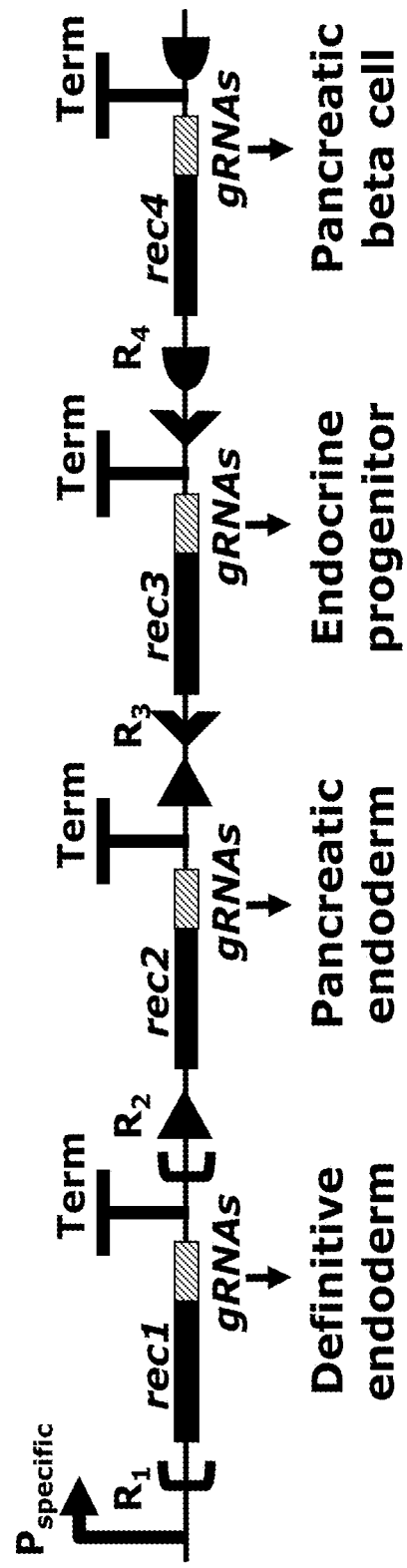

Directed differentiation of progenitor cells into insulin-producing pancreatic beta cells may be achieved using gene perturbation cassettes encoding gRNAs that activate expression of key transcription factors enabling the differentiation of the cell into definitive endoderm, pancreatic endoderm, endocrine progenitor, and then a pancreatic beta cell (FIG. 5B). As shown in FIG. 5B, expression of the first genetic perturbation cassette leads to expression of one or more gRNAs that activate expression of one or more transcription factors involved in the differentiation of the cell into definitive endoderm. Contact with a first inducer leads to excision of the first genetic perturbation cassette, allowing of expression of the second genetic perturbation cassette, including one or more gRNAs that activate expression of one or more transcription factors involved in the differentiation of the cell into pancreatic endoderm. Contact with a second inducer leads to excision of the second genetic perturbation cassette, allowing for expression of the third genetic perturbation cassette including one or more gRNAs that activate expression of one or more transcription factors involved in the differentiation of the cell into an endocrine progenitor cell. Contact with a third inducer leads to the excision of the third perturbation cassette, allowing for expression of the fourth genetic perturbation cassette, including one or more gRNAs that activate expression of one or more transcription factors involved in the differentiation of the cell to a pancreatic beta cell. Cellular differentiation or the cells state may be assessed (e.g., one or more cellular markers) can be assessed using methods known in the art prior to, during, and/or after contact with one or more inducers.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. In addition, any combination of two or more of such features, systems, articles, materials, kits, and/or methods, if such features, systems, articles, materials, kits, and/or methods are not mutually inconsistent, is included within the inventive scope of the present disclosure.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or," as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited. All references, patents and patent applications disclosed herein are incorporated by reference with respect to the subject matter for which each is cited, which in some cases may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United 30 States Patent Office Manual of Patent Examining Procedures, Section 2111.03.

What is claimed is:

1. A genetic construct comprising
a plurality of genetic perturbation cassettes,
wherein the plurality of genetic perturbation cassettes comprises
(a) a first genetic perturbation cassette comprising a first nucleic acid encoding
a first inducible recombinase comprising a first inducer-binding domain, wherein the activity of the first inducible recombinase is induced by interaction of the first inducer-binding domain with a first inducer,
a first gene element,
a first terminator, and
a first pair of recombinase recognition sites flanking the first inducible recombinase, the first gene element, and the first terminator, wherein the first inducible recombinase is capable of binding to and cleaving the first nucleic acid at each recombinase recognition site of the first pair of recombination recognition sites; and
(b) a second genetic perturbation cassette comprising a second nucleic acid encoding
a second inducible recombinase comprising a second inducer-binding domain, wherein the activity of the second inducible recombinase is induced by interaction of the second inducer-binding domain with a second inducer,
a second gene element,
a second terminator, and
a second pair of recombinase recognition sites flanking the second inducible recombinase, the second gene element, and the second terminator, wherein the second inducible recombinase is capable of binding to and cleaving the second nucleic acid at each recombinase recognition site of the second pair of recombination recognition sites; and
wherein the genetic construct further comprises a promoter located upstream of the first genetic perturbation cassette.

2. The genetic construct of claim 1 wherein the promoter is a cell-specific promoter or a cell state-specific promoter.

3. The genetic construct of claim 1,
wherein a nucleic acid encoding the first gene element is located within the 3' untranslated region of a nucleic acid encoding the first inducible recombinase, and/or a nucleic acid encoding the second gene element is located within the 3' untranslated region of a nucleic acid encoding the second inducible recombinase; or
wherein a nucleic acid encoding the first gene element is located within an intron of a nucleic acid encoding the first inducible recombinase, and/or a nucleic acid encoding the second gene element is located within an intron of a nucleic acid encoding the second inducible recombinase.

4. The genetic construct of claim 1, wherein the gene element is a nucleic acid encoding a protein, a gRNA, a miRNA, or a shRNA.

5. The genetic construct of claim 1, wherein the first inducible recombinase and/or the second inducible recombinase is selected from the group consisting of a tyrosine recombinase, a serine recombinase, and a split recombinase.

6. The genetic construct of claim 1, wherein one or more of the genetic perturbation cassettes of the plurality of genetic perturbation cassettes comprises one or more ribozyme sequence, and/or
one or more of the genetic perturbation cassettes of the plurality of genetic perturbation cassettes comprises one or more ribonuclease recognition sequences.

7. The genetic construct of claim 1, wherein one or more of the genetic perturbation cassettes of the plurality of genetic perturbation cassettes comprises one or more self-cleaving peptide sequences, optionally wherein the one or more self-cleaving peptide sequence is a P2A sequence.

8. The genetic construct of claim 1, wherein the plurality of genetic perturbation cassettes comprises one or more of the first genetic perturbation cassettes alternating with one or more of the second genetic perturbation cassettes.

9. The genetic construct of claim 1, wherein the plurality of genetic perturbation cassettes further comprises (c) a third genetic perturbation cassette comprising
a third nucleic acid encoding
a third inducible recombinase comprising a third inducer-binding domain, wherein the activity of the third inducible recombinase is induced by interaction of the third inducer-binding domain with a third inducer;
a third gene element;
a third terminator; and
a third part of recombinase recognition sites flanking the third inducible recombinase, the third gene element, and the third terminator, wherein the third inducible recombinase is capable of binding to and cleaving the third nucleic acid at each recombinase recognition site of the third pair of recombination recognition sites.

10. The genetic construct of claim 1, wherein the first and/or second inducer is a small molecule inducer, optionally wherein the small molecule inducer is a hormone, an antibiotic, or a synthetic ligand.

11. The genetic construct of claim 10, wherein the hormone is gibberellin (GIB) or abscisic acid (ABA);
the antibiotic is trimethoprim; or
the synthetic ligand is Shield-1 or 4-hydroxytamoxifen.

12. A vector comprising the genetic construct of claim 1.

13. A recombinant isolated cell comprising the genetic construct of claim 1.

14. The recombinant isolated cell of claim 13, further comprising a Cas6/Csy4 ribonuclease, and/or a Cas9 endonuclease.

15. The recombinant isolated cell of claim 13, wherein the cell is a bacterial cell, a fungal cell, a yeast cell, an insect cell, a plant cell, a non-human mammalian cell, or a human cell.

16. The recombinant isolated cell of claim 15, wherein the cell is a stem cell, optionally an embryonic stem cell or an induced pluripotent stem cell (iPS).

17. A transgenic non-human organism comprising a recombinant isolated cell of claim 13.

18. A method for assessing gene expression in a cell, comprising
(i) providing to a cell a genetic construct comprising a plurality of genetic perturbation cassettes,
wherein the plurality of genetic perturbation cassettes comprises
(a) a first genetic perturbation cassette comprising a nucleic acid encoding
a first inducible recombinase comprising a first inducer-binding domain, wherein the activity of the first inducible recombinase is induced by interaction of the first inducer-binding domain with a first inducer,
a gene element, a terminator, and
a first pair of recombinase recognition sites flanking the first inducible recombinase, the first gene element, and the first terminator, wherein the first inducible recombinase is capable of binding to and cleaving the nucleic acid at each recombinase recognition site of the first pair of recombination recognition sites; and
(b) a second genetic perturbation cassette comprising a nucleic acid encoding
a second inducible recombinase comprising a second inducer-binding domain, wherein the activity of the second inducible recombinase is induced by interaction of the second inducer-binding domain with a second inducer,
a second gene element,
a second terminator, and
a second pair of recombinase recognition sites flanking the second inducible recombinase, the second gene element, and the second terminator, wherein the second inducible recombinase is capable of binding to and cleaving the nucleic acid at each recombinase recognition site of the second pair of recombination recognition sites;
(ii) incubating the cell of (i) under conditions in which a first genetic perturbation cassette is expressed and the gene element is cleaved from the nucleic acid; and
(iii) assessing an output of one or more targets of the gene element.

19. The method of claim 18, wherein the plurality of genetic perturbation cassettes further comprises
(c) a third genetic perturbation cassette comprising a nucleic acid encoding
a third inducible recombinase comprising a third inducer-binding domain, wherein the activity of the third inducible recombinase is induced by interaction of the third inducer-binding domain with a third inducer,
a third gene element,
a third terminator, and
a third pair of recombinase recognition sites flanking the third inducible recombinase, the third gene element, and the third terminator, wherein the third inducible recombinase is capable of binding to and cleaving the nucleic acid at each recombinase recognition site of the third pair of recombination recognition sites.

20. The method of claim 18, wherein the output of one or more targets of the first, second, and/or third gene element involves assessing expression of the one or more targets.

\* \* \* \* \*

SEQUENCE LISTING

<160> NUMBER OF SEQ ID NOS: 5

<210> SEQ ID NO 1
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 1
gttcactgcc gtataggcag ctaagaaa                28

<210> SEQ ID NO 2
<211> LENGTH: 18
<212> TYPE: PRT
<213> ORGANISM: artificial sequence
<220> FEATURE:
<223> OTHER INFORMATION: synthetic polypeptide

<400> SEQUENCE: 2

Glu Gly Arg Gly Ser Leu Leu Thr Cys Gly Asp Val Glu Glu Asn Pro
1               5                   10                  15

Gly Pro

<210> SEQ ID NO 3
<211> LENGTH: 19
<212> TYPE: PRT
<213> ORGANISM: artificial sequence
<220> FEATURE:
<223> OTHER INFORMATION: synthetic polypeptide

<400> SEQUENCE: 3

Ala Thr Asn Phe Ser Leu Leu Lys Gln Ala Gly Asp Val Glu Glu Asn
1               5                   10                  15

Pro Gly Pro

<210> SEQ ID NO 4
<211> LENGTH: 20
<212> TYPE: PRT
<213> ORGANISM: artificial sequence
<220> FEATURE:
<223> OTHER INFORMATION: synthetic polypeptide

<400> SEQUENCE: 4

Gln Cys Thr Asn Tyr Ala Leu Leu Lys Leu Ala Gly Asp Val Glu Ser
1               5                   10                  15

Asn Pro Gly Pro
            20

<210> SEQ ID NO 5
<211> LENGTH: 22
<212> TYPE: PRT
<213> ORGANISM: artificial sequence
<220> FEATURE:
<223> OTHER INFORMATION: synthetic polypeptide

<400> SEQUENCE: 5

Val Lys Gln Thr Leu Asn Phe Asp Leu Leu Lys Leu Ala Gly Asp Val
1               5                   10                  15

Glu Ser Asn Pro Gly Pro
            20